United States Patent
Kufer et al.

(10) Patent No.: US 6,475,727 B1
(45) Date of Patent: Nov. 5, 2002

(54) PRIMERS AND METHODS FOR THE DETECTION OF DISSEMINATED TUMOR CELLS

(75) Inventors: Peter Kufer, Moosburg (DE); Alfred Zippelius, Munich (DE)

(73) Assignee: Micromet Gesellschaft Fur Biomedizinische Forschung mbH (DE)

( * ) Notice: Subject to any disclaimer, the term of this patent is extended or adjusted under 35 U.S.C. 154(b) by 0 days.

(21) Appl. No.: 09/402,690

(22) PCT Filed: Apr. 9, 1998

(86) PCT No.: PCT/EP98/02081

§ 371 (c)(1),
(2), (4) Date: Dec. 17, 1999

(87) PCT Pub. No.: WO98/46788

PCT Pub. Date: Oct. 22, 1998

(51) Int. Cl.[7] .................................. C12Q 1/68

(52) U.S. Cl. .................. 435/6; 435/91.2; 435/240.2; 435/69.1; 435/69.3; 435/172.3; 435/320.1; 435/235.1; 435/91.1; 536/23.5; 530/330; 935/9; 935/32; 935/34; 935/57; 935/62; 935/70; 935/71

(58) Field of Search .............. 435/6, 91.1, 91.2, 435/240.2, 69.1, 69.3, 172.3, 320.1, 235.1, 252.3; 536/23.5; 530/350; 935/9, 32, 34, 57, 62, 70, 71

(56) References Cited

FOREIGN PATENT DOCUMENTS

| | | |
|---|---|---|
| WO | WO 93 15221 A | 8/1993 |
| WO | WO 95 23874 A | 9/1995 |
| WO | WO 96 29430 A | 9/1996 |
| WO | WO 97 13858 A | 4/1997 |
| WO | WO 97 35589 A | 10/1997 |

OTHER PUBLICATIONS

Ezzell, C. Journal of NIH Research. "Cancer Vaccines: An Idea Whose Time Has Come?" 1995.*

Hoon, et al., "Detection of occult melanoma cells in blood with a multiple-marker polymerase chain reaction assay," *J. Clin. Oncol,*. 13:2109–2116 (1995).

Patard, et al., "Expression of Mage Genes in Transitional-Cell Carcinomas of the Urinary Bladder," *Int. J. Cancer*, 64:60–64 (1995).

Zippelius, et al., "Limitations of Reverse-Transcriptase Polymerase Chain Reaction Analyses for Detection of Micrometastatic Epithelial Cancer Cells in Bone Marrow," *J. Clin. Oncol.*, 15:2701–2708 (1997).

Zhai, et al., "Antigen-specific tumor vaccines. Development and characterization of recombinant adenoviruses encoding MART1 or gp100 for cancer therapy," *The Journal of Immunology*, 156:700–710 (1996).

Hu, et al., "Enhancement of Cytolytic T Lymphocyte Precursor Frequency in Melanoma Patients following Immunization with the MAGE–1 Peptide Loaded Antigen Presenting Cell-based Vaccine," *Cancer Research*, 56:2479–2483 (1996).

Alijagic, et al., "Dendritic cells generated from peripheral blood transfected with human tyrosinase induce specific T cell activation," *Eur. J. Immunol.*, 25:3100–3107 (1995).

Jaeger, et al., "Generation of Cytotoxic T–Cell Responses with Synthetic Melanoma–Associated Peptides In Vivo: Implications for Tumor Vaccines with Melanoma–Associated Antigens," *Int. J. Cancer*, 66:162–169 (1996).

Baurain et al., "High Frequency of Autologous Anti–Melanoma CTL Directed Against an Antigen Generated by a Point Mutation in a New Helicase Gene[1]," *The Journal of Immunology* 164:6057–6066 (2000).

Boël et al., "BAGE: a New Gene Encoding an Antigen Recognized on Human Melanomas by Cytolytic T Lymphocytes," *Immunity* 2:167–175 (1995).

Chaux et al., "Identification of MAGE–3 Epitopes Presented by HLA–DR Molecules to CD4[+] T Lymphocytes," *J. Exp. Med.* 189 (5):767–777 (1999).

Gaugler et al., "Human Gene MAGE–3 Codes for an Antigen Recognized on a Melanoma by Autologous Cytolytic T Lymphocytes," *J. Exp. Med* 179:921–930 (1994).

Herman et al., "A peptide encoded by the human MAGE3 gene and presented by HLA–B44 induces cytolytic T lymphocytes that recognize tumor cells expressing MAGE3," *Immunogenetics* 43:377–383 (1996).

Kawakami et al., "Identification of New Melanoma Epitopes on Melanosomal Proteins Recognized by Tumor Infiltrating T Lymphocytes Restricted by HLA–A1, –A2, and –A3 Alleles," *The Journal of Immunology* 161:6985–6992 (1998).

Kawakami et al., "Isolation of a New Melanoma Antigen, MART–2, Containing a Mutated Epitope Recognized by Autologous Tumor–Infiltrating T Lymphocytes[1.]" *The Journal of Immunology* 166:2871–2877 (2001).

(List continued on next page.)

Primary Examiner—W. Gary Jones
Assistant Examiner—Janell E. Taylor
(74) Attorney, Agent, or Firm—Gray Cary Ware & Freidenrich LLP

(57) ABSTRACT

The present invention relates to primers that specifically hybridize to nucleic acid molecules complementary to the messenger RNA transcribed from genes encoding MAGE tumor-specific antigens or a part thereof or to a complementary strand thereof encoding MAGE tumor specific antigens as well as to diagnostic compositions comprising said antigens. The present invention further relates to methods for detecting disseminated tumor cells employing the primers of the invention as well as methods for preparing a tumor adjuvant vaccine.

20 Claims, 17 Drawing Sheets

OTHER PUBLICATIONS

Lethé et al., "LAGE–1, A New Gene with Tumor Specificity," *Int. J. Cancer* 76:903–908 (1998).

Lucas et al., "MAGE–B5, MAGE–B6, MAGE–C2, and MAGE–C3: Four New Members of the MAGE Family with Tumor–Specific Expression," *Int. J. Cancer* 87:55–60 (2000).

Lucas et al., "Identification of a New MAGE Gene with Tumor–specific Expression by Representational Difference Analysis," *Cancer Research* 58:743–752 (1998).

Schultz et al., "A MAGE–A3 Peptide Presented by HLA–DP4 Is Recognized on Tumor Cells by $CD4^+$ Cytolytic Lymphocytes[1]," *Cancer Research* 60:6272–6275 (2000).

van der Bruggen et al., "A peptide encoded by human gene MAGE–3 and presented by HLA–A2 induces cytolytic T lymphocytes that recognize tumor cells expressing MAGE–3,*" *Eur. J. Immunol.* 24:3038–3043 (1994).

* cited by examiner

Figure 1:
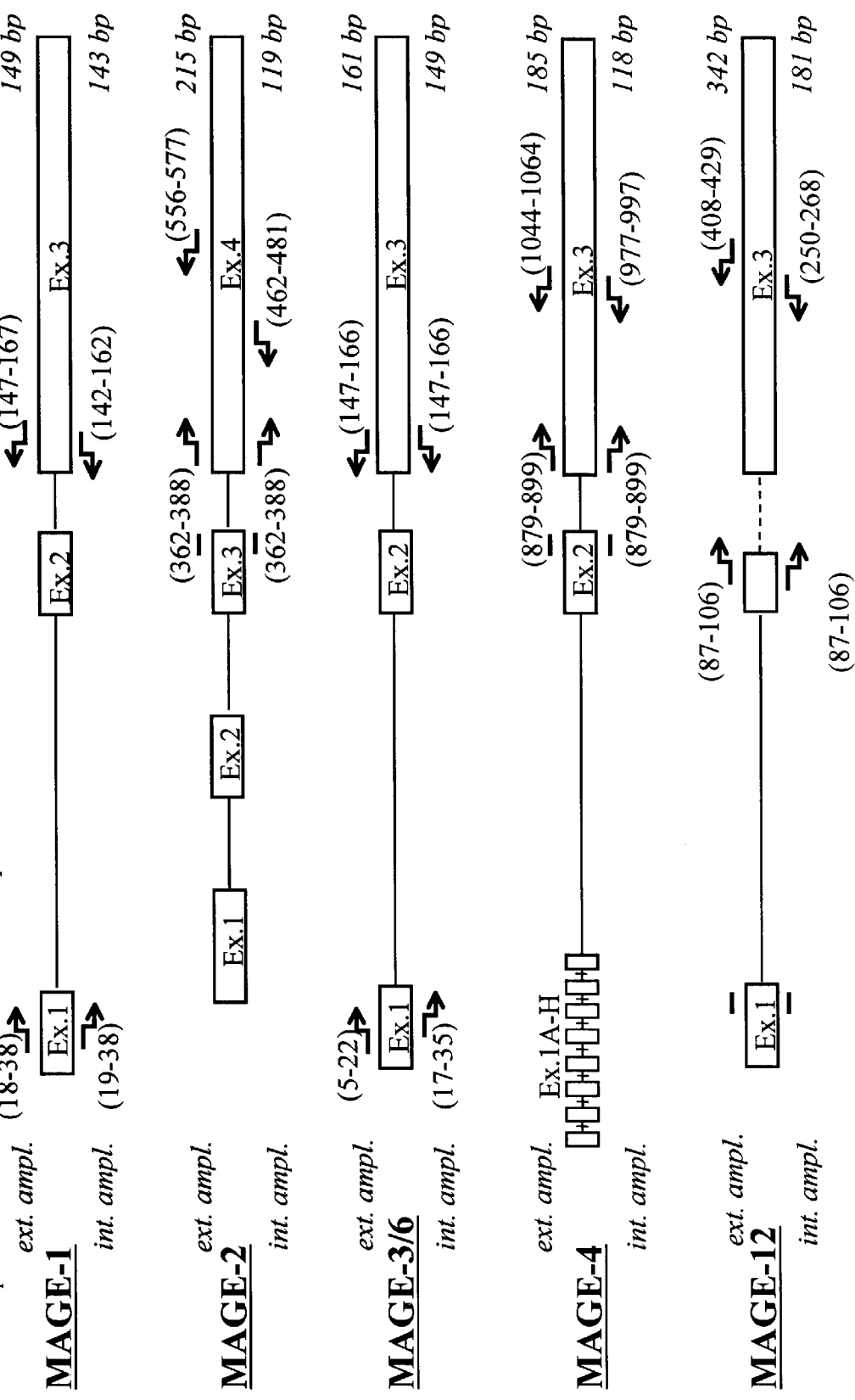

FIG. 1: Location of the specific oligonucleotide primers in the MAGE gene sequences. Grew boxes show the different exons. Arrows indicate the position of the oligonucleotides used for RT-PCR analyses. The expected size of the PCR products in the external as well as internal amplification is indicated.

Number of BM aspirates from lung carcinoma patients with positive results in PCR-assay for at least one MAGE and in CK-Immunocytochemistry:

Number of prostate carcinoma patients with positive results in PCR-assay for at least one MAGE and PSA, and in CK-Immunocytochemistry in BM of at least one aspiration site.

FIG. 4: Number of prostate carcinoma patients with positive results in PCR-assay for at least one Mage and PSA, and in CK- Immunocytochemistry in BM of at least one aspiration site.
a) analysis related to primary tumor
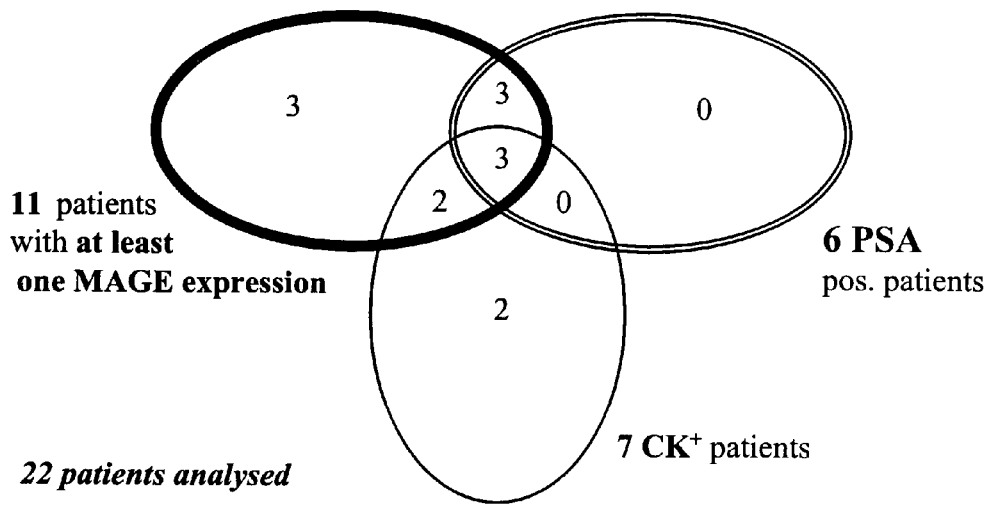
b) analysis related to progressive disease
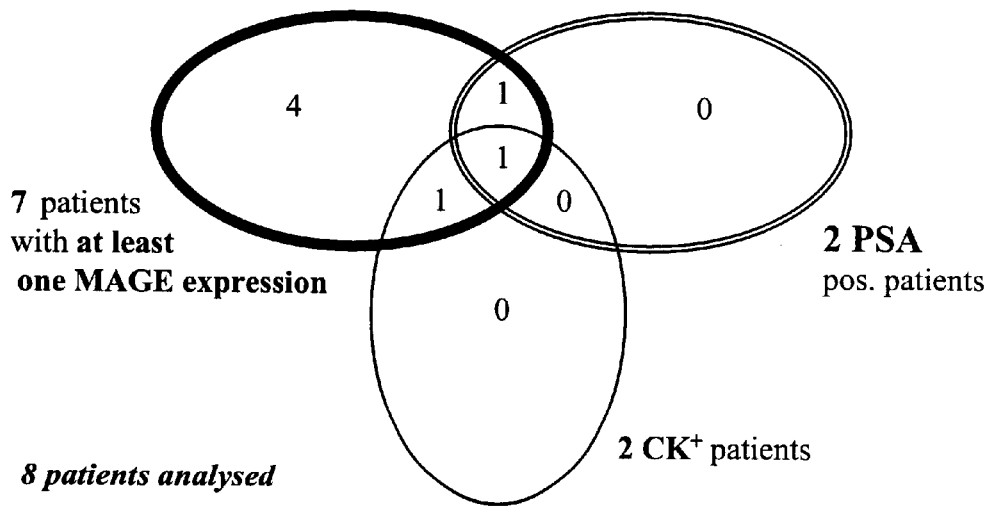

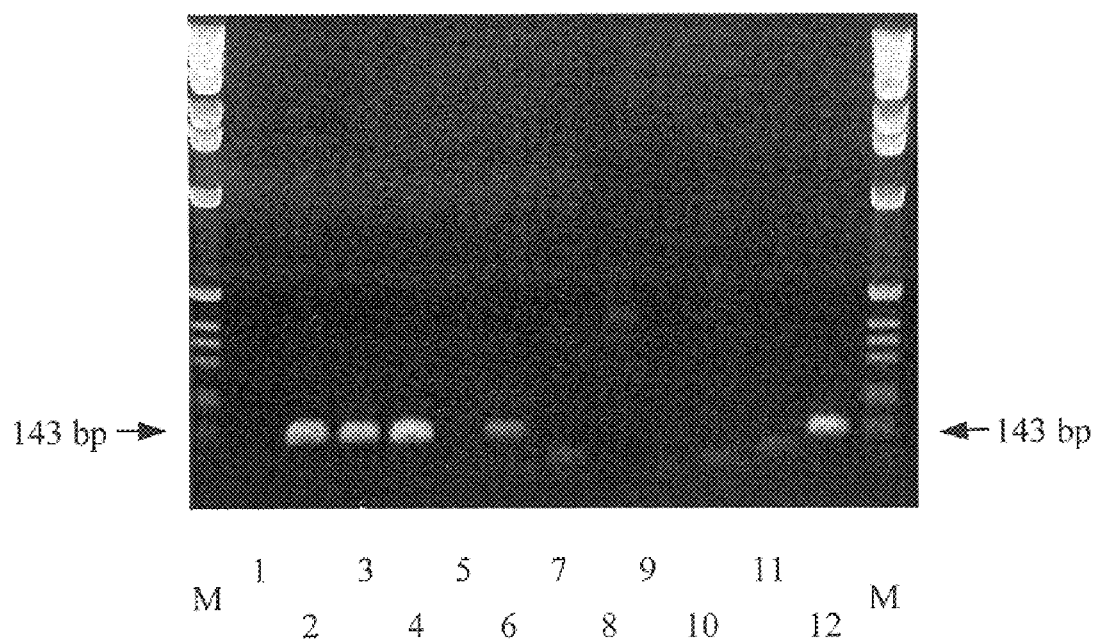

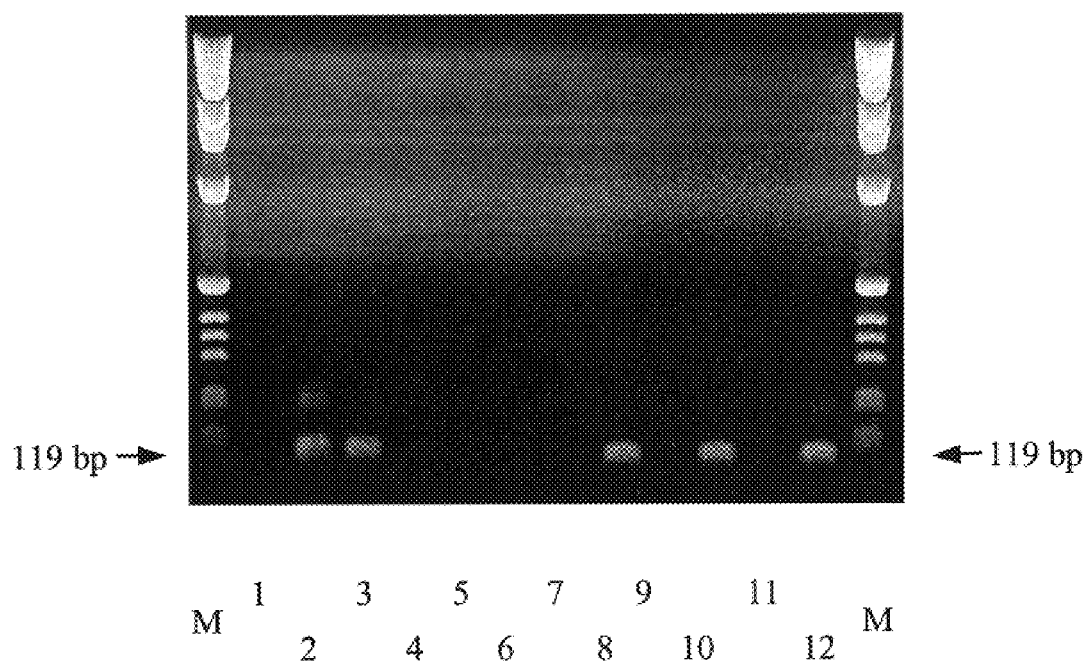

PRIMERS AND METHODS FOR THE DETECTION OF DISSEMINATED TUMOR CELLS

The present invention relates to primers that specifically hybridize to nucleic acid molecules complementary to the messenger RNA transcribed from genes encoding MAGE tumor-specific antigens or a part thereof or to a complementary strand thereof as well as to diagnostic compositions comprising said antigens. The present invention further relates to methods for detecting disseminated tumor cells employing the primers of the invention as well as methods for preparing a tumor adjuvant vaccine.

Immunotherapeutic approaches have previously been applied to patients with minimal residual disease and could reduce mortality and recurrence associated with distant metastases. Since early occult dissemination of tumor cells is already present in about half of the cancer patients, efficient treatment strategies have to be developed for eliminating residual tumor cells. Many immunocytochemical and PCR-based assays using histogenetic differentiation markers exclusively allow the detection of micrometastatic cells that worsen the prognosis after local tumorectomy without identifying antigens for adjuvant immunotherapy. Limitations of RT-PCR analyses in oncological disorders resulted in the tissue-specific rather than tumor-specific expression of marker genes. Detection of disseminated tumor cells is thus restricted to a few, certain tumor types deriving from similar histological origin. Moreover, tumor cells are only detectable in front of special tissue background, so that most published approaches depend on samples taken from mesenchymal compartments. The presence of ubiquitous transcriptional factors and minimal activation of promotor sequences in background cells may cause illegitimate transcription and reduce specificity and sensitivity due to competing background signals. Furthermore, most assays measure only a single marker gene not considering inter- and intra-individual tumor cell heterogenity.

Several tumor rejection antigens have recently been characterized that are presented on major histocompatibility complex (MHC) class I molecules to autologous cytolytic T-lymphocytes (CTL). The MAGE genes belong to a family of 12 closely related genes with an overall homology of 64–85% and are classified as "cancer-testis-antigens".

The MAGE genes have been employed in the prior art to use primers specific for MAGE 1 to 4, 6 and 12 for the detection of a variety of tumors (WO 95/23874). The specific primers as well as the regions they prime to in the MAGE genes are, however, inappropriate for the diagnosis of disseminated tumor cells in human samples. WO 96/29430 discloses genetic markers for the detection of melanomas and breast cancer cells including occult cancer cells or metastatic cells derived therefrom. In said application, it is further described that a number of markers including MAGE-3 may be employed to detect such tumors. However, methods disclosed in this application are not expected to be suited for the detection of disseminated tumor cells derived from human malignacies of many different histological origins.

Since, in particular, the early reliable detection of disseminated tumor cells in a patient enables the early treatment and/or vaccination in order to prevent recurrence of cancerous growth, the technical problem underlying the present invention was to improve the sensitivity of the prior art methods for detecting such disseminated tumor cells in patients with maligancies of many different histological origins. The solution to said problem is achieved by the embodiments characterized in the claims.

Accordingly, the present invention relates to a primer specifically hybridizing to a nucleic acid molecule complementary to the messenger RNA transcribed from a gene encoding a MAGE tumor-specific antigen or a part thereof or to a complementary strand thereof, said primer being selected from the group of (i) primers having the same 3' portion as one of the following groups of primers:

(a)
| | |
|---|---|
| 5'-gtagagttcggccgaaggaac-3' | (SEQ ID NO: 1) |
| 5'-caggagctgggcaatgaagac-3' | (SEQ ID NO: 2) |
| 5'-cattgaaggagaagatctgcct-3' | (SEQ ID NO: 3) |
| 5'-gagtagaagaggaagaagcggt-3' | (SEQ ID NO: 4) |
| 5'-gaagccggcccaggctcg-3' | (SEQ ID NO: 5) |
| 5'-gatgactctggtcagggcaa-3' | (SEQ ID NO: 6) |
| 5'-caccaaggagaagatctgcct-3' | (SEQ ID NO: 7) |
| 5'-tcctcagtagtaggagcctgt-3' | (SEQ ID NO: 8) |
| 5'-tccgtgaggaggcaaggttc-3' | (SEQ ID NO: 9) |
| 5'-atcggattgactccagagagta-3' | (SEQ ID NO: 10) |

(b)
| | |
|---|---|
| 5'-tagagttcggccgaaggaac-3' | (SEQ ID NO: 11) |
| 5'-ctgggcaatgaagacccaca-3' | (SEQ ID NO: 12) |
| 5'-cattgaaggagaagatctgcct-3' | (SEQ ID NO: 13) |
| 5'-caggcttgcagtgctgactc-3' | (SEQ ID NO: 14) |
| 5'-ggctcggtgaggaggcaag-3' | (SEQ ID NO: 15) |
| 5'-gatgactctggtcagggcaa-3' | (SEQ ID NO: 16) |
| 5'-caccaaggagaagatctgcct-3' | (SEQ ID NO: 17) |
| 5'-caggcttgcagtgctgactct-3' | (SEQ ID NO: 18) |
| 5'-tccgtgaggaggcaaggttc-3' | (SEQ ID NO: 19) |
| 5'-gagcctgcgcacccaccaa-3' | (SEQ ID NO: 20) | and;

(ii) primers that overlap with a primer sequence depicted in (a) or (b).

The term "overlap" in this context means the overlap of at least one nucleotide.

Accordingly, said primers can hybridize to RNA, preferably mRNA or to DNA, preferably cDNA.

In accordance with the present invention, it was found that the primers having the above-recited 3' ends are particularly useful in detecting disseminated tumor cells of many different histological origins at a sensitivity level that was unknown from the prior art. Additionally, primers that overlap with the above-recited nucleic acid sequences and that hybridize to MAGE genes have been found useful for the detection of disseminated tumor cells in human samples. Preferably, said primers overlap with the nucleic acid sequences depicted under (a), above. It is further preferred that the primers of the invention have a length of between 15 and 25 nucleotides. With the exception of primers that recognize MAGE-3 and -6, each of said primers specifically detects the expression of only one MAGE gene.

The present invention accordingly provides a means for detecting a cancerous condition at a very early stage of the disease and thus allows the timely treatment of patients where disseminated tumor cells are detected. It was surprisingly found by the present invention that, in contrast to prior art reports, disseminated tumor cells of many different histological origins can be detected using the above-recited primers, even if the analyzed patient has no clinical evidence of disease. It has to be emphasized that the prior art methods and primers as well as the regions of the MAGE genes to which the primers described in the prior art hybridize are not suitable for detecting disseminated tumor cells in samples of patients with malignancies of many different histological origins since the sensitivity of said primers has, in accordance with the present invention, proven not to be high enough for such an analysis. The term "specifically hybridizing" as used in accordance with the present invention is intended to mean that these primers do not cross-amplify nucleic acids from the genes of other MAGE tumor specific antigens in a sensitive RT-PCR. Such RT-PCRs can be devised by the person skilled in the art according to conventional protocols. The specific hybridization occurs under stringent conditions. Such conditions can be devised by the person skilled in the art without undue burden according to conventional protocols; see, e.g., "Nucleic Acid Hybridization, A Practical Approach"; edited by Hames & Higgins, IRL Press, Oxford 1985.

The primers of the invention are advantageously used in PCR amplification of nucleic acid sequences derived from the desired MAGE genes or fragments thereof. The primers of the invention are devised to avoid the amplification of genomic DNA but to amplify a DNA sequence derived from the reverse transcription of messenger RNA. In this way, the PCR product can be unambiguously correlated with expressed MAGE-genes. PCR may be carried out according to conventional methods. Also, the PCR product may be detected according to protocols that are established in the art.

Preferably, the primer of the invention is a primer depicted in either group (a) or group (b), supra.

The primers of this embodiment have been particularly useful and advantageous in identifying disseminated tumor cells in samples of patients with malignancies of many different histological origins. It is also particularly preferred that primers of group (a) are used as primers for a first round of PCR amplification whereas primers of group (b) are used in a nested primer PCR amplification.

The present invention further relates to a diagnostic composition comprising at least four primers according to the invention wherein said at least four primers hybridize pair-wise to strands of opposite orientation of at least two different nucleic acid molecules wherein strands of one orientation are complementary to the messenger RNA transcribed from the genes of at least two different MAGE tumor-specific antigens.

The diagnostic composition of the invention is particularly useful for carrying out a variety of PCRs and thus for unambiguously identifying the presence of disseminated tumor cells in patients with malignancies of many different histological origins. As has been found in accordance with the present invention, at least two different MAGE-genes from the group of MAGE-1,-2,-3,-4,-6 and -12 should be checked for expression in order to further secure the diagnostic value of the investigation. Preferably, said diagnostic kit comprises at least one pair of primers specific for each of the MAGE-1,-2,-3,-4,-6 and -12 genes. It is further preferred that the analysis of the sample is carried out with the kit of the invention until the expression of at least two different MAGE-genes has been secured.

The bottling of the primers in said kit is effected according to conventional procedures. Preferably, each primer is separately bottled. Alternatively, the primers specific for each MAGE-gene are bottled together with the understanding that primers for a primary and a nested primer reaction are separately bottled.

The present invention further relates to a method of detecting disseminated tumor cells indicative of a cancerous condition in a patient comprising:

(a) carrying out PCR on cDNA obtained from mRNA from one or more patient samples using at least two primers of the invention hybridizing pair-wise to strands of opposite orientation of at least two one cDNA molecule wherein strands of one orientation are complementary to the messenger RNA transcribed from the genes of at least one MAGE tumor-specific antigen; and (b) detecting one or more PCR products.

The term "cancerous condition" is intended to mean the whole spectrum from the initiation of malignant transformation in single cells to advanced cancer disease including distant solid metastasis.

Preferably, at least four primers specific for at least two MAGE transcripts and complementary strands thereof are employed in the method of the invention.

Additionally, the present invention relates to a method of preparing a tumor adjuvant vaccine comprising the following steps:

(a) carrying out PCR on cDNA obtained from mRNA from one or more patient samples using at least four primers of the invention hybridizing pair-wise to strands of opposite orientation of at least two different nucleic acid molecules wherein strands of one orientation are complementary to the messenger RNA transcribed from the genes of at least two different MAGE tumor-specific antigens;

(b) detecting resulting PCR products; and (c) using at least one MAGE-gene product, expression of said MAGE-gene being detected as a result of step (b) for preparing an adjuvent tumor vaccine based on MAGE-antigen-derived peptides resembling MHC-restricted T-cell-epitopes, whole MAGE-antigens or fragments thereof, MAGE-transfected host cells, DNA vaccinating strategies using MAGE-encoding nucleotide sequences or any other immunization method based on MAGE-gene products or their coding nucleotide sequences.

This embodiment of the invention relates to the direct application of the positive analysis of the presence of disseminated tumor cells in a human sample. Once said tumor cells have been detected, a suitable antidote for the further proliferation of said tumor cells eventually resulting in tumorous growth should be devised. The method of the present invention provides such an antidote. The tumor adjuvant vaccine can be prepared according to conventional protocols. In particular, it is envisaged to pulse dendritic cells isolated from the patient with peptides derived from the coding sequences of those MAGE-genes detected to be expressed by the disseminated tumor cells of this particular patient using the diagnostic composition of the present invention, these peptides being suited for binding to MHC-molecules of this patient thus resembling MHC-restricted T-cells epitopes. The peptide-pulsed dendritic cells will then be reinjected into the patient and will migrate to the T-cell zones of secondary lymphoid organs where they prime MAGE-specific T-lymphocytes thus resulting in an immune response against MAGE-positive tumor cells.

In a preferred embodiment of the method of the invention, said cDNA is obtained by:
(a) preparing mRNA from one or more samples removed from said patient; and
(b) reverse transcribing said mRNA.

The preparation of said mRNA and the reverse transcription thereof is conveniently effected by conventional procedures.

Reverse transcription of mRNA resulting in the corresponding cDNA may be carried out by random hexanucleotide priming as described in Example 3 by oligo-dT-priming or by specific priming using one or more oligonucleotides complementary to oneor more MAGE-mRNA species. Due to the high degree of sequence homology among different members of the Mage gene family, specific primers for the cDNA-synthesis may be identified that efficiently hybridize to the mRNA of more than one Mage gene and most preferably to all the Mage genes used according to the present invention (Mage-1, -2, -3/6, -4 and -12). Such "pan-Mage primers" can be identified and tested according to the state of the art especially represented by computer based sequence analysis and laboratory manuals e.g. Sambrook (Molecular Cloning; A Laboratory Manual, 2nd Edition, Cold Spring Harbour Laboratory Press, Cold Spring Harbour, N.Y. (1989)) or Hames & Higgins (Nucleic acid hybridization; A practical approach, IRL Press, Oxford/Washington D.C. (1985)).

In an additional preferred embodiment of the method of the invention, said PCR is nested PCR.

As has been found in accordance with the present invention, the nested PCR is a further safeguard for obtaining unambiguous results with regard to the patient's disease status.

In a further preferred embodiment of the method of the invention, said primers hybridize to 2 to 6 different nucleic acid molecules complementary to the messenger RNA transcribed from the genes of MAGE tumor-specific antigens and to complementary strands thereof.

In a further preferred embodiment of the method of the invention, said MAGE tumor-specific antigens are the MAGE-1, -2, 3, -4, -6 or -12 tumor specific antigens.

Of all MAGE antigens, the above-recited antigens most often appear on tumor cells, as was found in accordance with the present invention, and are therefore particularly indicative of the risk of cancer to develop metastatic tumors.

It is further preferred in accordance with the present invention to remove samples from two different aspiration sites. As was found in accordance with the present invention, the analysis of double-sided aspiration significantly improves sensitivity. It is therefore advisable to use double-sides aspiration in the routine diagnosis of tumor cell dissemination.

In a further preferred embodiment of the method of the invention, said samples to be analyzed are bone marrow aspirates.

As has been surprisingly found in accordance with the present invention, the use of bone marrow aspirates as a source for analyzing the metastatic potential of a patient is more sensitive than using peripheral blood as suggested by the prior art.

Additionally preferred is a method wherein said mRNA preparation comprises the following steps:
(a) immediately lysing the sample in buffer essentially completely avoiding RNA-degradation; and
(b) optionally centrifuging the mRNA obtained in the lysate through a cushion of an RNAse-inhibiting agent, preferably cesium trifluoracetate.

This embodiment of the invention is advantageous since it precludes the loss of mRNA that is, as is well known in the art, sensitive to degradation by exonucleases and therefore precludes loss of sensitivity of the assay method. Further, said method reduces heme concentrations in the RNA-preparation below values inhibiting Taq-polymerase. This is because hemoglobin is removed, high heme concentrations decreasing the sensitivity of the assay method.

The term "immediately" means that the sample is lysed within seconds after removal from the patient in an agent depicted under (a). Said agent is preferably a guanidine salt such as guanidine isothiocyanate. After lysis of the sample, said sample is overlaid on a cushion of an RNAse-inhibiting agent depicted under (b). Said agent is preferably a cesium salt such as caesium trifluoroacetate. The mRNA is advantageously obtained by ultracentrifugation through said cushion.

Preferably, the cancerous condition is related to prostate cancer, non-small or small cell lung cancer or sarcoma or malignant melanoma or breast cancer or colorectal cancer. The above enumeration of tumor types is to be understood as a selection of tumors that is recited as preferred examples. Other tumors may be also detected in their early stages in accordance with the present invention.

The figures show:

FIG. 1: Location of the specific oligonucleotide primers in the MAGE gene sequences. Grey boxes show the different exons. Arrows indicate the position of the oligonucleotides used for RT-PCR analyses. The expected size of the PCR products in the external as well as internal amplification is indicated.

Figure 2:
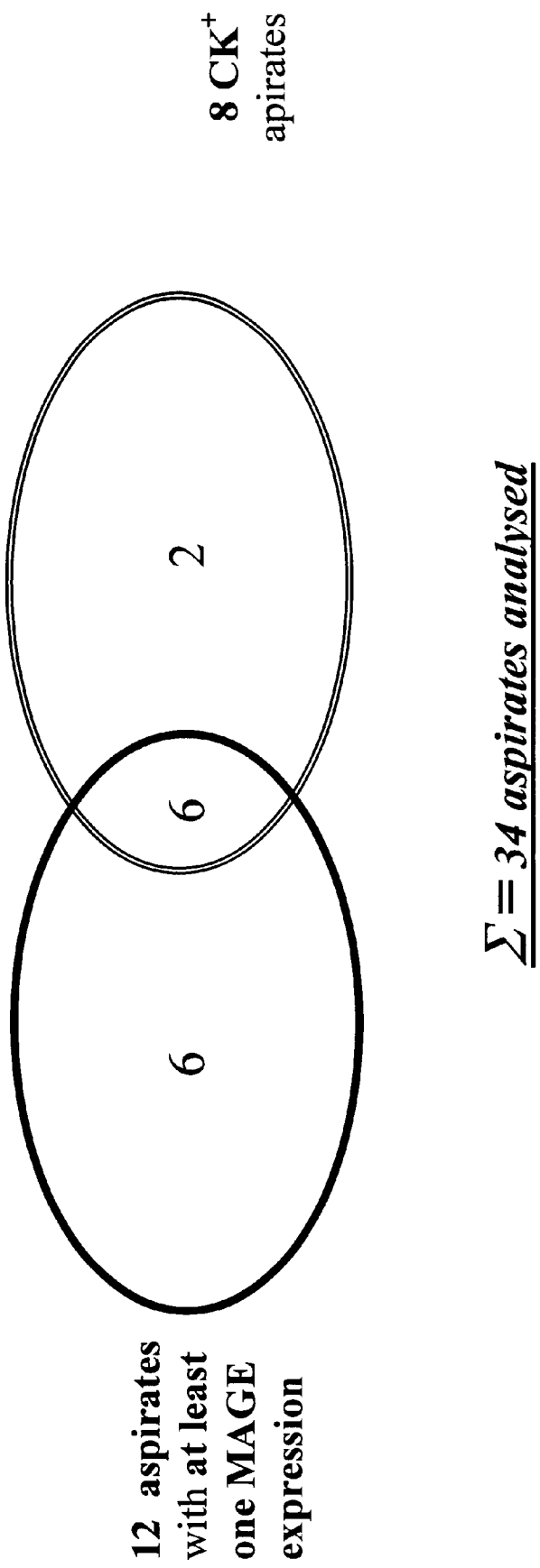

FIG. 2: Number of BM aspirates from lung carcinoma patients with positive results in PCR-assay for at least one MAGE and CK-Immunocytochemistry.

Figure 3:
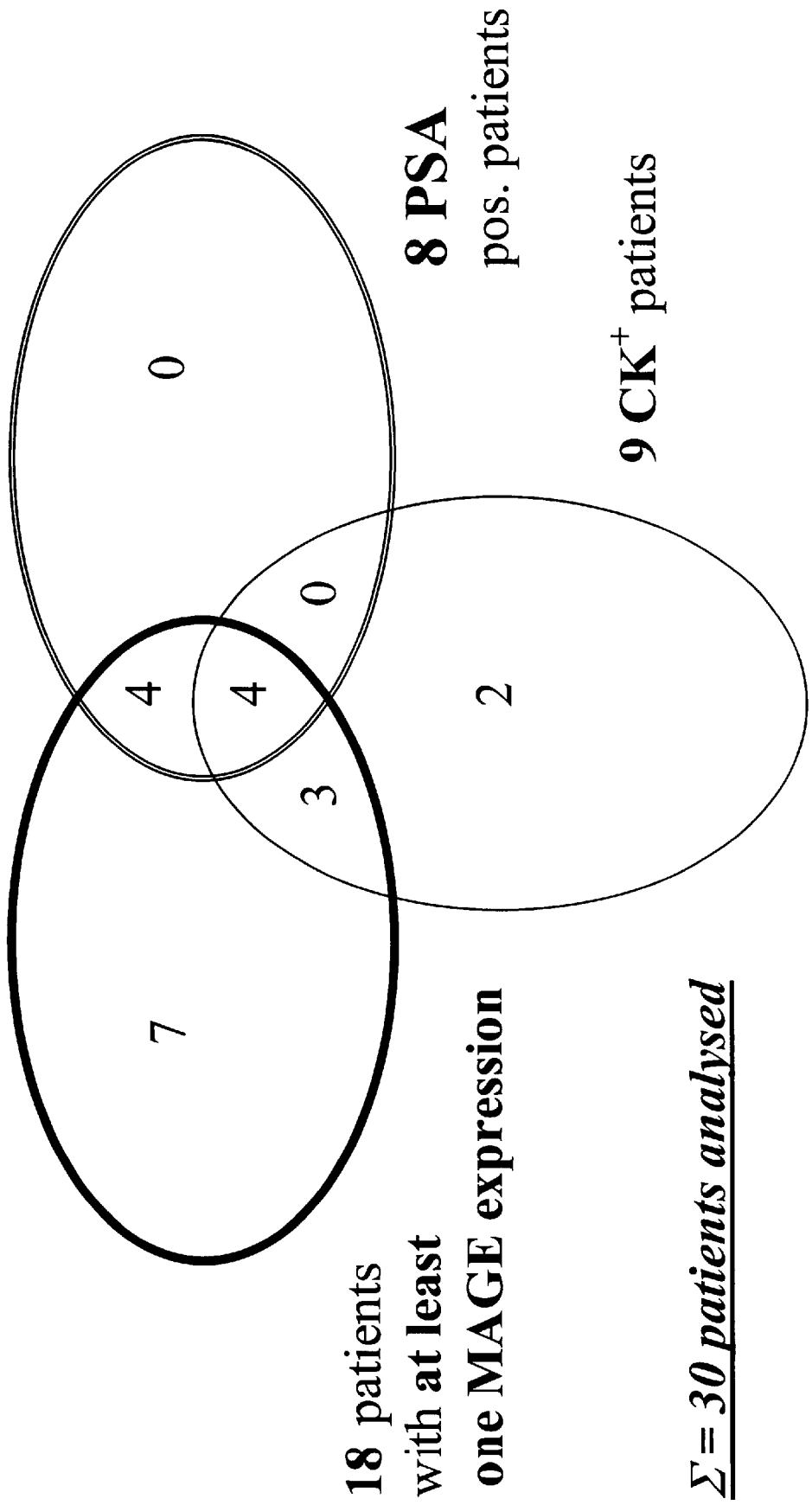

FIG. 3: Number of prostate carcinoma patients with positive results in PCR-assay for at least one MAGE and PSA, and in CK-Immunocytochemistry in BM of at least one aspiration site.

FIG. 4: Number of prostate carcinoma patients with positive results in PCR-assay for at least one MAGE and PSA, and in CK-Immunocytochemistry in BM of at least one aspiration site.
a) analysis related to primary tumor
b) analysis related to progressive disease FIG. 5: Mage-1 PCR assay of bone marrow samples from lung cancer patients. Patient samples 1–8 (ZI.JO., BA.MA., DE.IV., NE.WI., HO.FR., MA.JO., RE.LU., HE.JO) in lane 4–11. Controls: mock preparation in lane 1, 10 Mz-2Mel tumor cells in 1 ml blood in lane 2, 100 Mz-2Mel tumor cells in 1 ml blood in lane 3, 1000 Mz-2Mel tumor cells in 1 ml blood in lane 12. DNA ladder in lane M.

FIG. 6: Mage-2 PCR assay of bone marrow samples from lung cancer patients. Patient samples 1–8 (FI.RI., RE.LU., KU.LU., KL.JU., HE.JO., HA.AN., RO.AD., BE.FR.) in lane 4–11. Controls: mock preparation in lane 1, 10 Mz-2Mel tumor cells in 1 ml blood in lane 2, 100 Mz-2Mel tumor cells in 1 ml blood in lane 3, 1000 Mz-2Mel tumor cells in 1 ml blood in lane 12. DNA ladder in lane M.

Figure 7:
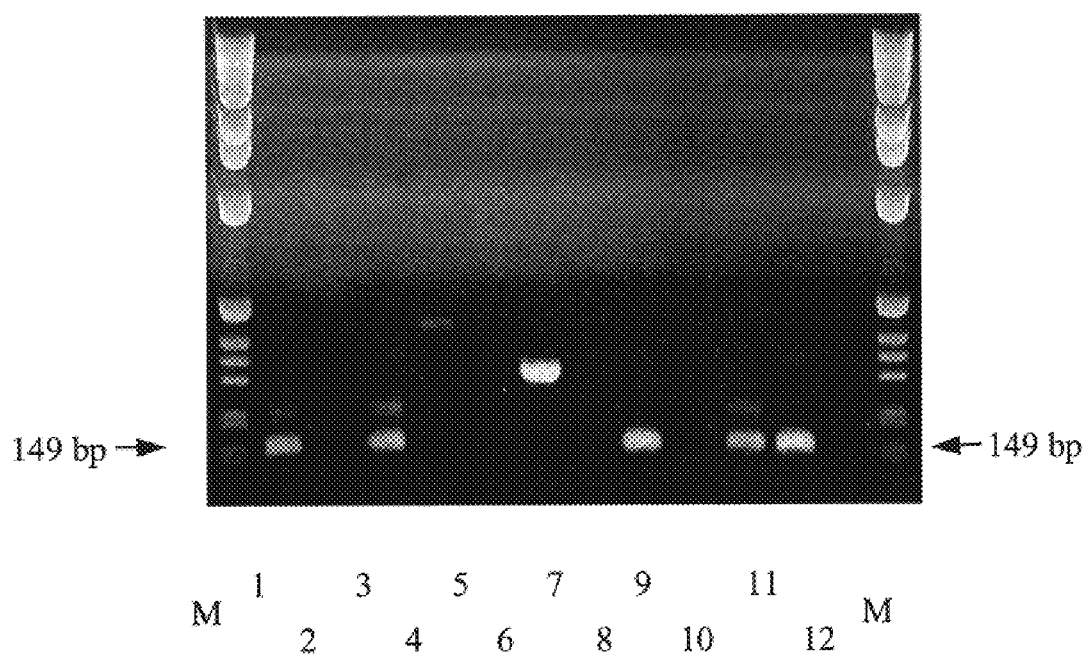

FIG. 7: Mage-3 PCR assay of bone marrow samples from lung cancer patients. Patient samples 1–8 (HA.HI., DE.IV., HO.FR., MA.RO., LA.AL., AR.JO., VO.KL., WE.AL.) in lane 4–11. Controls: mock preparation in lane 1, 10 Mz-2Mel tumor cells in 1 ml blood in lane 2, 100 Mz-2Mel tumor cells in 1 ml blood in lane 3, 1000 Mz-2Mel tumor cells in 1 ml blood in lane 12. DNA ladder in lane M.

Figure 8:
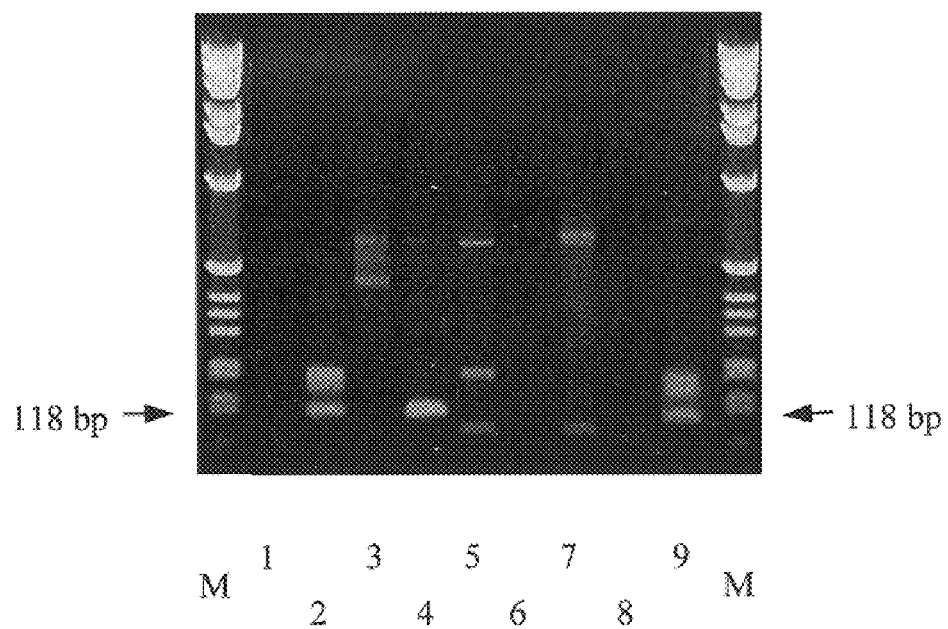

FIG. 8: Mage-4 PCR assay of bone marrow samples from lung cancer patients. Patient samples 1–6 (HA.AN., VO.KL., DE.IV., BE.FR., LA.BR., IN.FR..) in lane 3–8. Controls: mock preparation in lane 1, 10 LB23-SAR tumor cells in 1 ml blood in lane 2, 100 LB23-SAR tumor cells in 1 ml blood in lane 9, DNA ladder in lane M.

Figure 9:
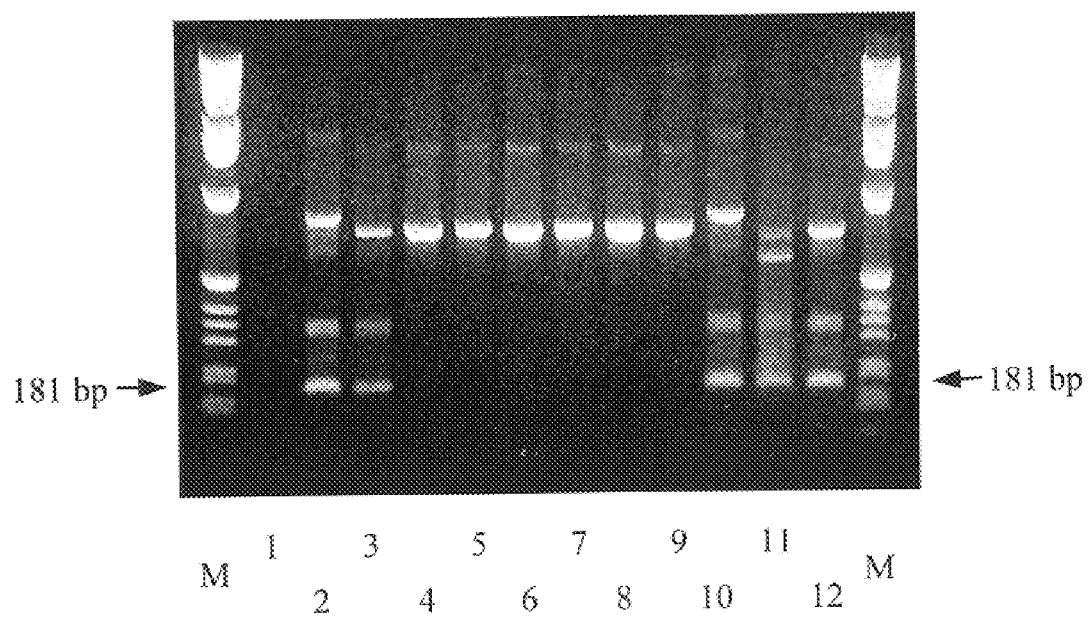

FIG. 9: Mage-12 PCR assay of bone marrow samples from lung cancer patients. Patient samples 1–8 (SO.JO., HA.HI., HO.FR., MA.JO., LA.BR., IN.FR., NI.OS. FI.RI.) in lane 4–11. Controls: mock preparation in lane 1, 10 Mz-2Mel tumor cells in 1 ml blood in lane 2, 100 Mz-2Mel tumor cells in 1 ml blood in lane 3, 1000 Mz-2Mel tumor cells in 1 ml blood in lane 12. DNA ladder in lane M.

Figure 10:
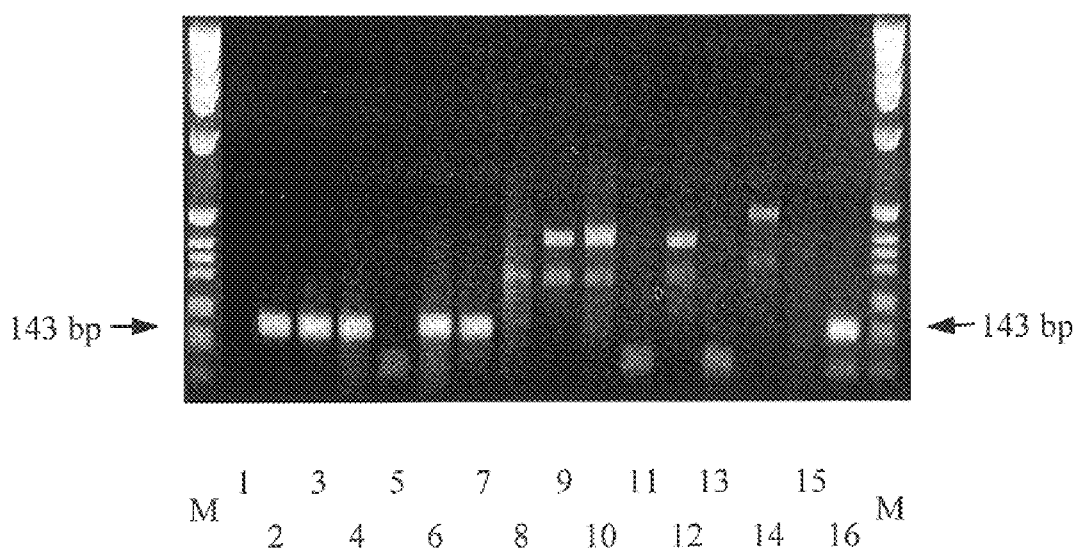

FIG. 10: Mage-1 PCR assay of bone marrow samples from prostate cancer patients and healthy persons. Patient samples 1–8 (FE.KU.re., RI.ER.le., ZO.JO.re., SC.HO.le., KN.DI.re., MA.GU.le., ME.JO.le., BE.WA.le.) in lane 4–11. Healthy persons in lane 12–15. Controls: mock preparation in lane 1, 10 Mz-2Mel tumor cells in 1 ml blood in lane 2, 100 Mz-2Mel tumor cells in 1 ml blood in lane 3, 1000 Mz-2Mel tumor cells in 1 ml blood in lane 16. DNA ladder in lane M.

Figure 11:
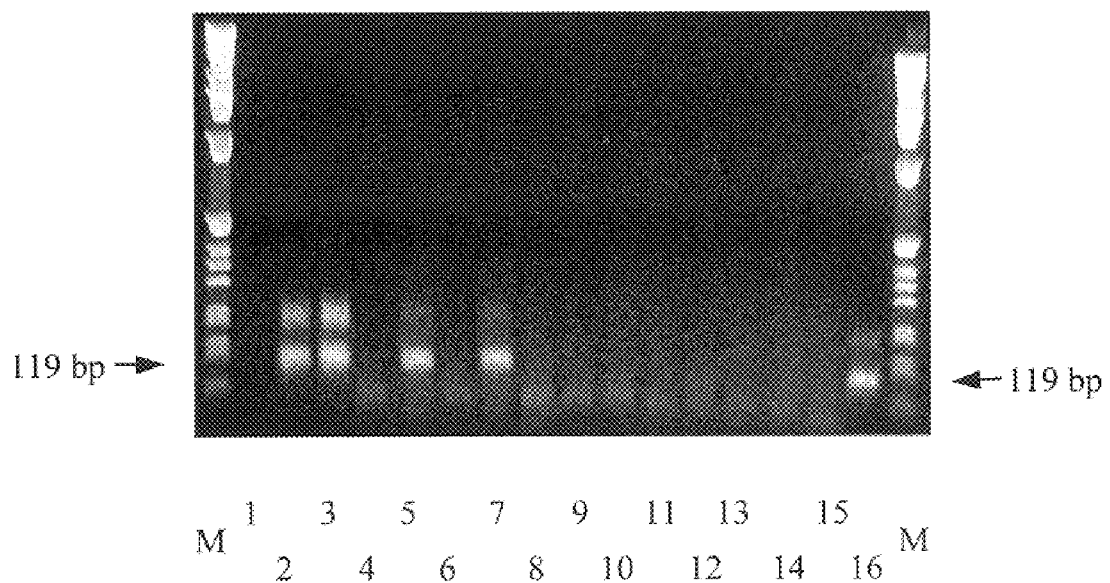

FIG. 11: Mage-2 PCR assay of bone marrow samples from prostate cancer patients and healthy persons. Patient samples 1–8 (SC.GU.le., WO.JA.re., PF.LO.le., SC.AU.le., FE.KU.le., ZO.JO.le., ST.EB.le., SC.HO.le.) in lane 4–11. Healthy persons in lane 12–15. Controls: mock preparation in lane 1, 10 Mz-2Mel tumor cells in 1 ml blood in lane 2, 100 Mz-2Mel tumor cells in 1 ml blood in lane 3, 1000 Mz-2Mel tumor cells in 1 ml blood in lane 16. DNA ladder in lane M.

Figure 12:
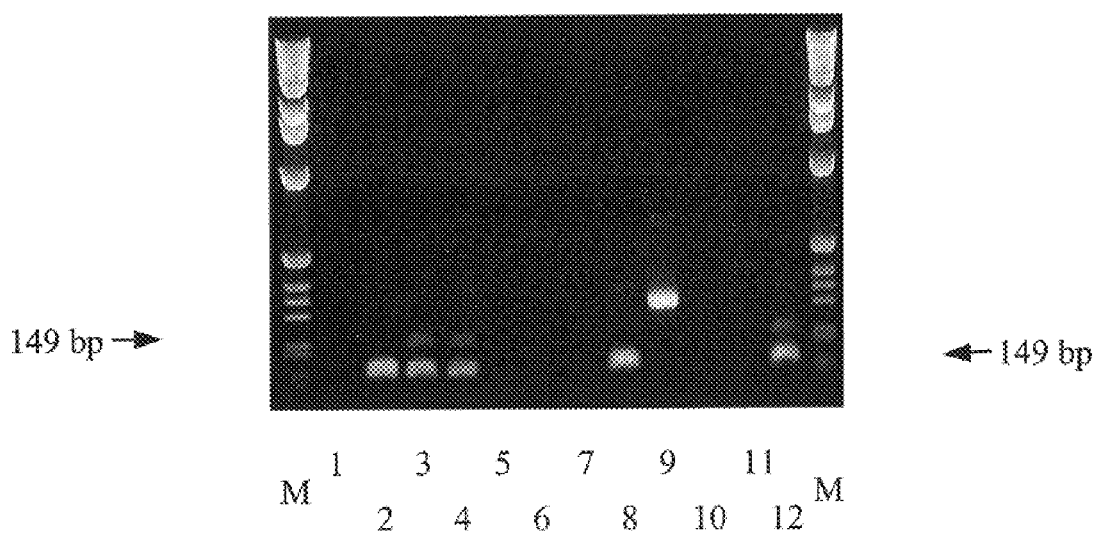

FIG. 12: Mage-3 PCR assay of bone marrow samples from prostate cancer patients. Patient samples 1–8 (RI.ER.le., SC.GU.le, BA.GI.re., BE.WA.le, WO.JA.le., FE.KU.re., KN.DI.re., RI.FE.re.) in lane 4–11. Controls: mock preparation in lane 1, 10 Mz-2Mel tumor cells in 1 ml blood in lane 2, 100 Mz-2Mel tumor cells in 1 ml blood in lane 3, 1000 Mz-2Mel tumor cells in 1 ml blood in lane 12. DNA ladder in lane M.

Figure 13:
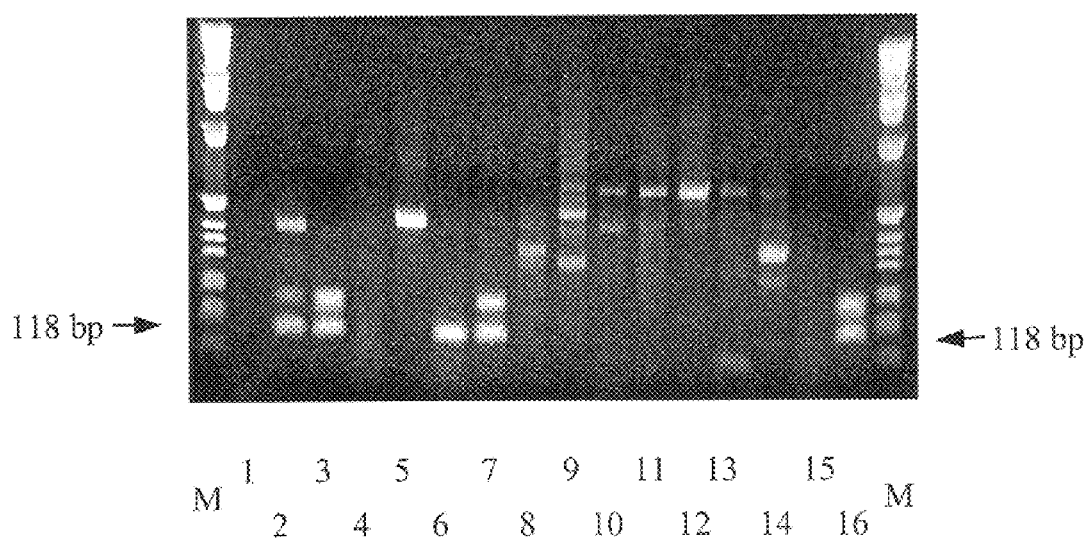

FIG. 13: Mage-4 PCR assay of bone marrow samples from prostate cancer patients and healthy persons. Patient samples 1–8 (PF.LO.le., HI.ER.le., SC.HO.re., HE.RU.re., LU.VO.le., MA.GU.le., WI.JA.le., LE.DI.re.) in lane 4–11. Healthy persons in lane 12–15. Controls: mock preparation in lane 1, 10 LB23-SAR tumor cells in 1 ml blood in lane 2, 100 LB23-SAR tumor cells in 1 ml blood in lane 3, 1000 LB23-SAR tumor cells in 1 ml blood in lane 16. DNA ladder in lane M.

Figure 14:
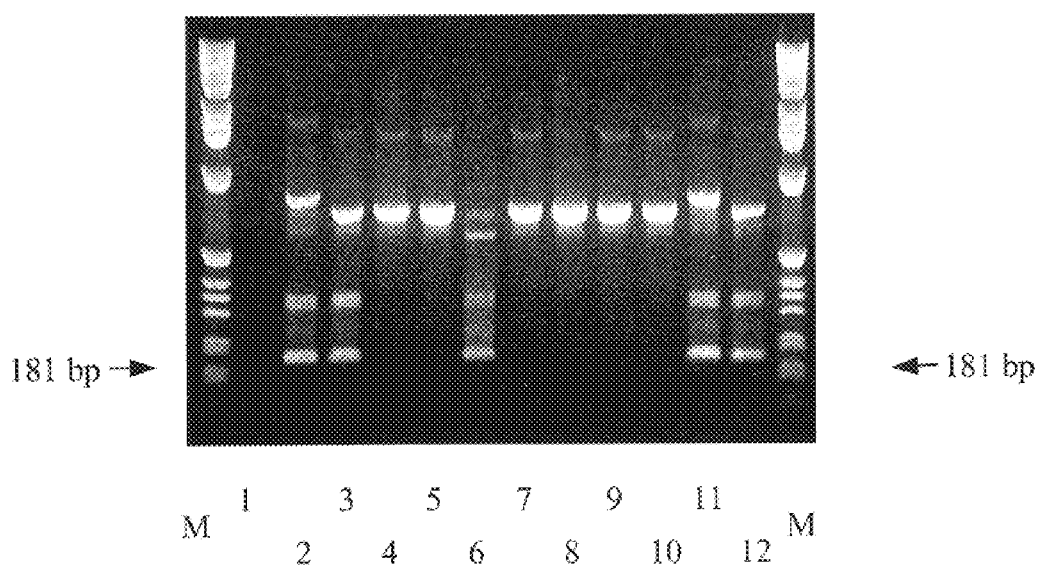

FIG. 14: MAGE-12 PCR assay of bone marrow samples from prostate cancer patients. Patient samples 1–8 (WO.JA.le., RI.ER.le., LU.VO.re., GE.CH.le., BA.GI.re., WE.HJ.le., HI.ER.le., BI.GU.re.) in lane 4–11. Controls: mock preparation in lane 1, 10 Mz-2Mel tumor cells in 1 ml blood in lane 2, 100 Mz-2Mel tumor cells in 1 ml blood in lane 3, 1000 Mz-2Mel tumor cells in 1 ml blood in lane 12. DNA ladder in lane M.

Figure 15A:
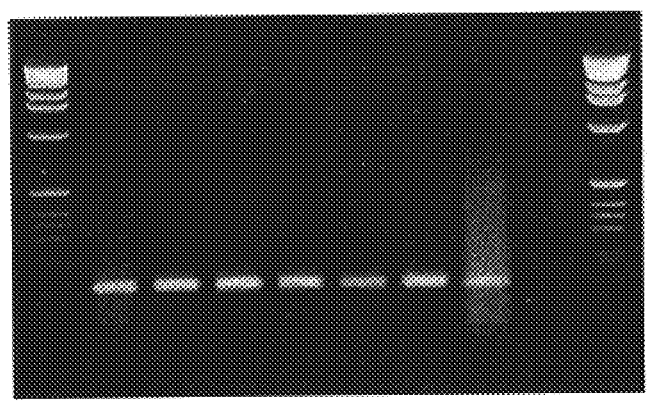
Figure 15B:
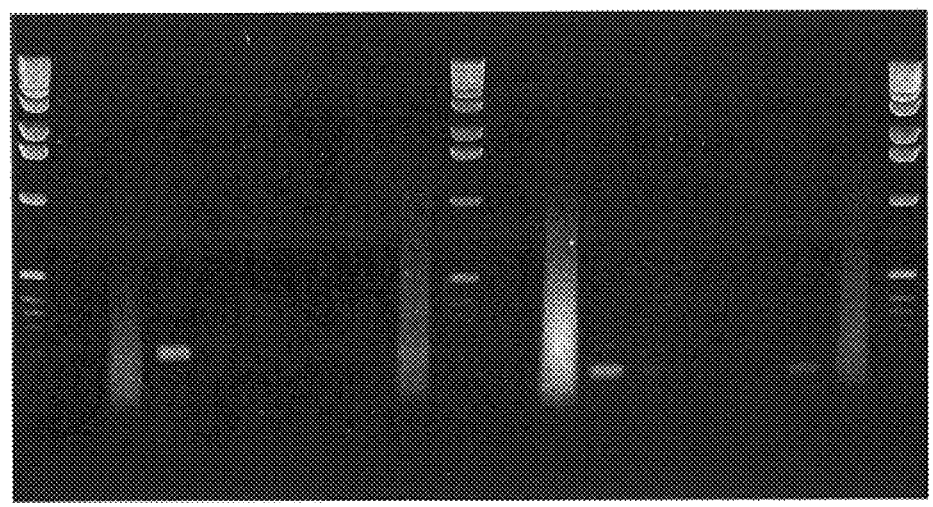
Figure 15C:
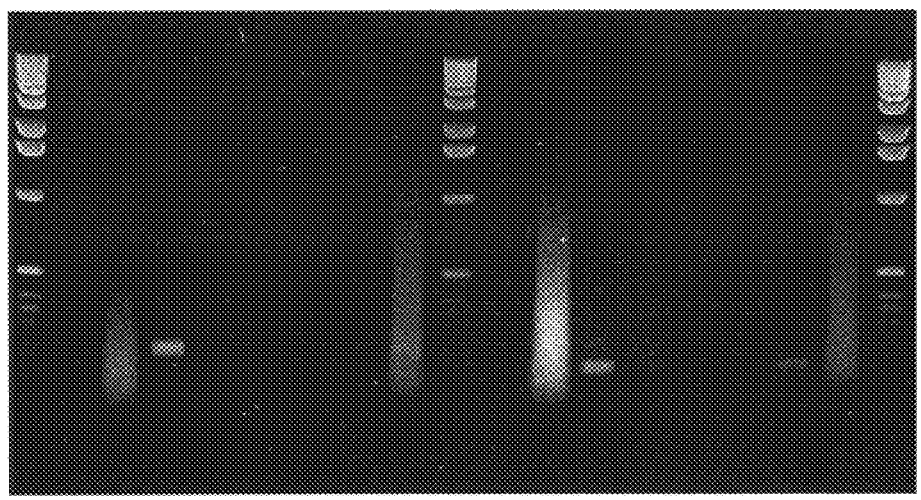

FIG. 15: MAGE PCR assay of primary tumor of sarcoma patient H.M.; (see also Table 4c) PCR assays were performed in quadruplicates. (a) Expression of MAGE-1. Tumor samples in lane 3–6. Controls: mock preparation in lane 8, tumor cell line Mz-2Mel in lane 1, 6, 7. DNA ladder in lane M. (b) Expression of MAGE-2 and -3. Corresponding to Mage-2, tumor samples in lane 4–7, tumor cell line Mz-2Mel in lane 2, 3 and 8, mock preparation in lane 1. Corresponding to MAGE-3, tumor samples in lane 12–15, tumor cell line Mz-2Mel in lane 10, 11, and 16, mock preparation in lane 9. DNA ladder in lane M. (c) Expression of MAGE -4 and -12. Corresponding to MAGE-4, tumor samples in lane 4–7, tumor cell line LB23-SAR in lane 2,3 and 8, mock preparation in lane 1. Corresponding to MAGE-12, tumor samples in lane 12–15, tumor cell line Mz-2Mel in lane 10,11, and 16, mock preparation in lane 9. DNA ladder in lane M.

The examples illustrate the invention.

EXAMPLE 1

Cell lines and Patients

In total, 28 tumor cell lines were tested for MAGE expression. Out of them 17 were of epithelial (MCF-7, BT20, SkBr3, MDA-MB: breast; LNCaP: prostate, SkCo, HT29, LS180, SW480: colon; A498, Caki I: kidney; HepB3, HepG2: liver; Panc-Tu: pancreas; Kato: stomach, A427: lung and A431: skin) and 2 were of mesenchymal origin (HT1080, LB23-SAR). 3 hematopoietic (U937, Raji,K562) and 6 tumor cell lines derived of neuroectodermal tissue (A172, U138: glioblastoma; Mel-Juso, Mel-Mei, A375, Mz-2Mel: melanoma) were analyzed. The melanoma cell line Mz-2Mel and the sarcoma cell line LB23-SAR were gifts of Francis Brasseur (Ludwig Institute, Brussels). The study population consisted of double-sided BM aspirates of 30 patients with prostate cancer (n=60 aspirates); single-sided BM aspirates were taken from 34 patients with non-small and small lung cancer (n=34 aspirates) and 6 patients with sarcoma (n=6 aspirates). Further, we analyzed peripheral blood samples from 12 patients with prostate cancer (n=12 samples), 6 patients with sarcoma (n=6 samples) and 12 patients with malignant melanoma (n=12 samples). All patients with prostate and lung cancer were staged as free of distant overt metastases (MO). In contrast, patients with sarcoma and malignant melanoma were suffering from advanced disease or metastases in different organs. Patients were graded by histopathological examination and staged according to the TNM-classification (4th edition, 1987). To test the specificity of the MAGE PCR assays, a "negative" control group consisting of 67 non-malignant patients: 20 BM aspirates and 20 peripheral blood samples with a history of trauma, benign tumors, inflammatory diseases or healthy donors were admitted to the study; furthermore, bone marrow of 27 healthy allogeneic bone marrow donors were analyzed with regard to expression of Mage gene products. Using heparine as an anticoagulant, BM was aspirated from one or two sides of the upper iliac crest under local anesthesia in patients with prostate cancer and sarcoma while chemotherapy or under general anesthesia in patients with lung cancer prior to tumorectomy.

EXAMPLE 2

Tissue Sampling and Preparation

To avoid degradation of the RNA, 1 ml of the native sample was immediately within seconds mixed with 5 ml nucleic acid extraction buffer (4 M guanidine isothiocyanate, 0.5% sarcosyl (N-laurylsarcosine sodium salt), 25 mM sodium citrate, pH=7.0) and 0.7% 2-mercaptoethanol. After vigorous vortexing the sample could easily and without risk of RNA degradation be stored at −20° C. until needed. For purifying total RNA the method of Okayama et al. was modified as follows: The lysate was gently overlaid onto a 5 ml cushion of CsTFA-solution (cesium trifluoracetate (Pharmacia, Freiburg, Germany) and 0.25 M EDTA, pH=7.0) in diethyl pyrocarbonate (DEPC)-treated, autoclaved SW40 centrifuge tubes and centrifuged at 35,000 rpm for 18 h at 15° C. After centrifugation, the upper layer of nucleic acid extraction buffer/BM or blood mixture and the lower layer of CsTFA-solution were removed by aspiration and discarded. The tubes were quickly inverted, placed on a paper towel to drain for 2 minutes, and the bottom 1 cm of the tube was cut off with a scalpel. The bottom was turned over again, placed on a bed of ice and the RNA pellet was dissolved in a total of 300 μl DEPC-treated HPLC-water. Sequentially, the sample was transferred to a fresh tube with 300 μl of a phenol-chloroform-isoamylalcohol mixture (25:24:1, vol:vol:vol). Again after vortexing and centrifugation (1 min, 14,000 rpm) the upper phase was reextracted with 300 μl chloroform. Subsequentially, the RNA was precipitated with 300 μl isopropanol, 40 μl 3M sodium acetate, pH=5.0 and 20 μg glycogen at −20° C. over night. After centrifugation the RNA pellet was washed with 70% ethanol, dried for 4 minutes and dissolved in 5 μl DEPC-treated HPLC-water. To determine the sensitivity of the PCR assay, Mz-2Mel and LB23-SAR were harvested from tissue culture flasks, single cells of these lines were picked with a pipette under the microscope and mixed in 1 ml peripheral blood of a healthy donor. RNA preparation was also performed as described above. To minimize the potential of PCR carryover all samples were processed at a site separate from amplification and electrophoresis of PCR products.

EXAMPLE 3

Reverse-transcriptase Polymerase Chain Reaction

Half of total RNA was denatured for 5 min at 70° C., quickly chilled on ice and was reverse transcribed using random hexamer primers (Boehringer Mannheim, Mannheim, Germany). The synthesis was carried out with a First-strand cDNA synthesis kit (Gibco, Eggenstein, Germany), including Superscript II (Gibco) in a final volume of 10 μl containing 50 mM Tris (pH=8.3), 75 mM Kcl, 3 mM $MgCl_2$, 10 mM DTT, 0.5 mM total dNTP, 1.6 μg of the random primers and 100 units Superscript II. After the addition of RNA, the samples were incubated at 40° C. for 1 hour and subsequently diluted with 10 μl HPLC-water.

PCR-reaction mixture (10 μl) was composed of 1 μl cDNA, 1 μl of 10×PCR buffer (100 mM Tris, pH=8.3, 500 mM KCl, 10 mM $MgCl_2$), 40 μM dNTP, 0.4 μM of each of the two primers, 5 μg BSA (Boehringer Mannheim, Mannheim, Germany), 0.6 units of Taq DNA-Polymerase (Boehringer Mannheim, Mannheim, Germany) and overlaid with 12.5 μl of mineral oil. The primers for the MAGE genes were designed from previously published sequences (Tab. 1, FIG. 1), and were selected to maximize mismatches between the different MAGE-sequences particularly in the 3'-region in order to avoid cross-amplification. Specific PCR assays were possible for MAGE genes 1,2,4 and 12 since the percentage of identity of these genes varies between 64 to 85%. In contrast, the sequence of Mage-6 was found to be 99% identical to that of Mage-3. Therefore our primers for Mage-3/6 hybridize to both genes and PCR can detect Mage-3 and/or Mage-6 expression. Short primers in the range of 19–22 bases and annealing temperatures of about 60° C. were most efficient. Also junction primers spanning over two exons showed surprising results in efficiency. As published recently, we applied primers for PSA (Tab. 1) on exons 2 and 3 that span a 1.6-kilobase intron and amplify three different PSA cDNAs. To confirm the presence of cDNA template in each sample, primers specific for p53 (kindly provided by Thomas Blankenstein, München, Tab. 1) were used to coamplify this ubiquitously expressed "housekeeping" gene. Oligonucleotide primers were synthesized and purified at Genset, Paris. For the external fragment amplification of the MAGE PCR assays following cycling profile was used: denaturation at 94° C. for 6 min, annealing at 60° C. for 30 sec and extension at 72° C. for 2 min for the first cycle; denaturation at 93° C. for 40 sec, annealing at 60° C. for 30 sec and extension at 72° C. for 20 sec for 14 cycles; denaturation at 93° C. for 40 sec, annealing at 60° C. for 30 sec and extension at 72° C. for 30 sec for 50 cycles; terminal extension at 72° C. for 2 min and cooling at 30° C. for 1 min.

One microliter of the reaction was then transferred into a second tube containing the PCR mixture described above. For the nested fragment amplification thirty more cycles were run at 93° C. (40 sec), 58° C. (30 sec) and 72° C. (30 sec) with a final extension at 72° C. for 2 min and cooling at 30° C. for 1 min. The cycling conditions for PSA varied by using conventional one-stage PCR and separating the 14 cycles into 7 cycles with and annealing-temperature of 64° C. and 7 cycles with 57° C., continuing 50 cycles with 57° C. The amplification was performed on a Hybaid Thermal Reactor (Biometra, Göttingen, Germany) using plate control. Importantly, all pipetting was performed on ice under a laminar air-flow bench with filtered pipette tips, external and nested fragment amplification were performed in different rooms to avoid potential DNA cross-contaminations. Negative control reactions (mock reactions) for the RNA preparation and RT-PCR were performed routinely. PCR products were analyzed on 1.8% agarose by gel electrophoresis and by direct visualization after ethidium bromide staining under UV-light. A 1 kb DNA ladder (Gibco BRL, Eggenstein, Germany) was used as a reference marker for all assays. The specificity of the amplification products obtained was monitored with DNA sequencing. Using this approach, the RT-PCR assays for the different MAGE genes could detect 10 cells of a malignant tumor cell line mixed with 1 ml normal whole blood. Reproducibility of the nested PCR assay was 100%.

EXAMPLE 4

Immunocytochemistry

After removal of 1 ml of whole BM and blood for PCR analyses, mononuclear cells (MNC) from the remaining aspirate were isolated by density gradient centrifugation through Ficoll-Hypaque (Pharmacia, Freiburg, Germany) at 400 g for 30 minutes, interface cells were cytocentrifuged onto glass slides at 150 g for 5 minutes ($5\times10^5$ cells per slide). BM specimens were stained with monoclonal antibodies CK2 (kindly provided by Dr. M. Osborn, Max Planck Institut Göttingen, and later obtained from Dr. H. Bodenmüller, Boehringer Mannheim, Tutzing, Germany; these as well as all other antibodies used in the experimental part of the application were prepared according to conventional procedures. The specific antibodies used here are not essential for carrying out the invention) and A-45-B/B3 (kindly provided by Micromet GmbH, Martinsried, Germany), which detect common epitopes on cytokeratin components. The antibody reactions were developed with the alkaline phosphatase anti-alkaline phosphatase (APAAP) technique combined with the Neufuchsin method for visualizing antibody binding. Briefly, after incubation with the primary antibody, a polyvalent rabbit anti-mouse Ig antiserum (Z259, Dako, Hamburg, Germany), and performed complexes of alkaline phosphatase and monoclonal anti-alkaline phosphatase antibodies (D651, Dako, Hamburg, Germany) were used at the dilutions recommended by the manufacturer (Dakopotts, Hamburg, Germany). For each BM aspirate, two slides containing a total of 106 MNC were evaluated

EXAMPLE 5

Expression of MAGE Genes in Normal Bone Marrow and Blood Versus Other Markers

RNA was extracted from BM of control patients and subjected to RT-PCR amplification using primers from several histogenetic differentiation markers and tumor-associated antigens (Tab. 2). After 50 cycles of amplification, product of all these candidate genes known to be expressed in malignancies was seen except PSA and MAGE genes. Nevertheless, PSA expression is restricted to malignancies of the prostate and seems to be downregulated in a fraction of disseminated tumor cells. In contrast, MAGE genes are ubiquitously expressed in malignancies and no amplification product after sensitive nested PCR was seen in any of the analyzed 20 BM aspirates and 20 peripheral blood samples. This result was confirmed when analyzing bone marrow aspirates of 27 healthy persons. None of said aspirates from the allogenic bone marrow donors expressed the MAGE genes, see Table 5.

The highly restricted expression pattern of tumor antigens in contrast to tumor-associated molecules strongly supports that MAGE genes may be interesting candidates for PCR-based detection of minimal residual disease.

EXAMPLE 6

Expression of MAGE Genes in Bone Marrow Samples of Patients with Different Types of Tumors The objective of the study was to establish a PCR assay for detection of disseminated tumor cells of different histological origin. Since primary tumors show a heterogenous expression pattern for different MAGE genes (1,2,3,4,6,12), as shown for prostate cancer in Table 6, we initially evaluated our multimarker RT-PCR assay in vitro and screened 28 cell lines of epithelial, mesenchymal, hematopoietic and neuroectodermal origin (Tab. 3). Performing one-stage PCR with 35 cycles, 27 of 28 cell lines exhibited expression of at least one MAGE and therefore scored positive in the PCR. Only one renal cell carcinoma (A498) was completely negative. Increasing the sensitivity by performing 65 cycles A498 showed MAGE-2 and -4 expression. This heterogenous expression pattern of the MAGE genes together with the complete absence of expression in normal hematopoietic tissue encouraged us to evaluate BM aspirates and peripheral blood samples from patients suffering from malignancies of different histological origin. Results and patient characteristics are listed in Table 4a–c and Table 7. Gelelectrophoresis of Mage PCR products is shown in examples in FIGS. 5 to 14.

Prostate Cancer

First, BM aspirates were obtained from both sites of the iliac crest of patients with prostate cancer (Tab. 4a, Tab. 7). Out of the 30 patients transcripts of MAGE-1 were observed in 12 patients (40%), MAGE-2 in 3 pat. (17%), MAGE-3/6 in 5 pat. (17%), MAGE-4 in 6 pat. (20%) and MAGE-12 in 5 pat. (17%). The overall positivity for expression of at least one MAGE gene in one patient was 18 (60%). Interestingly, only two patients showed concordant expression pattern of MAGE genes in both aspiration sites, while 16 patients displayed heterogenous expression. There was no correlation between the primary tumor stage, the histopathological grading or the mean PSA concentration in serum and the MAGE-positivity in the PCR-assay.

Lung Cancer

The second epithelial tumor entity we were interested in was non-small and small lung cancer (Tab. 4b). We analyzed single-sided BM aspirates of 34 carcinoma patients with positive results for MAGE-1 in 5 asp. (15%), MAGE-2 in 4 asp. (12%), MAGE-3/6 in 3 asp. (9%), MAGE-4 in 3 asp. (9%) and MAGE-12 in 4 asp. (12%). At least one MAGE expression was found in 12 asp. (35%). MAGE-PCR displayed positive signals in 7 of 19 BM aspirates of patients with squamous cell carcinoma and 3 of 10 analyzed BM aspirates of patients with adenocarcinoma.

Sarcoma

Since mesenchymal tumor cell lines express different MAGE genes, we analyzed single-sided BM aspirates of 6 sarcoma patients staged as M1 using the sensitive MAGE PCR assays (Tab. 4c). 5 samples showed at least expression of one MAGE gene, while MAGE 1,2,4,12 were positive in two tumor samples, respectively, and MAGE-3/6 was positive in one sample. Transcripts of all MAGE genes were found in BM aspirates of patient T.C., suffering from rhabdomyosarcoma with infiltrating bone metastases.

EXAMPLE 7

Correlation of MAGE Expression with Other Tumor Cell Dissemination Markers

All BM aspirates of patients with malignancies of the lung and prostate were evaluated by both the MAGE RT-PCR and the well established immunocytochemical assay using mAb against cytokeratins. Expression of at least one MAGE gene and CK-status of 34 analyzed lung carcinoma samples is displayed in FIG. 2. 12 aspirates showed positive results in MAGE PCR assay, while 8 aspirates revealed CK positive cells. 6 aspirates were found to be concordant positive and were all taken from patients with squamous cell carcinoma. MAGE PCR showed positive results in 3 of 10 patients with adenocarcinoma, while immunocytochemistry exhibited no CK-positive cells in this histological subtype.

Further, patients with prostate carcinoma were analyzed using MAGE RT-PCR, CK-immunocytochemistry and a third assay: a sensitive RT-PCR for PSA. FIG. 3 shows the results of PCR assays for MAGE and PSA, and of CK-immunocytochemistry. As mentioned above, out of 30 patients with prostate carcinoma 18 patients showed expression for at least one MAGE gene. PSA expression was observed in 8 patients, while CK-immunostained cells were found in 9 patients. Interestingly, all PSA positive patients and seven of nine CK-positive patients were confirmed by positive results of the MAGE PCR assay. Comparatively, CK-immunostained cells were found only in four PSA-positive patients. Moreover, seven PSA- and CK-negative patients revealed MAGE expression as indicator for disseminated tumor cells.

EXAMPLE 8

Expression in Blood Samples Compared to Bone Marrow Samples

Most of recently published PCR assays claim to detect circulating tumor cells and predict high sensitivity; nevertheless the results of the analyses of PB samples obtained with CK-immunocytochemistry are disappointing. We analyzed 18 blood samples of patients with prostate carcinoma (n=12) and sarcoma (n=6), that were taken in parallel to the BM aspiration. As listed in Table 4a, MAGE-1 and MAGE-3/6 transcripts were found in one patient, while MAGE-4 expression could be observed in two patients with prostate cancer. Interestingly, two patients with MAGE expression in blood exhibited a different pattern in bone marrow. PSA-PCR assay was completely negative for all analyzed PB samples. The obviously lower sensitivity of the assay using peripheral blood was confirmed by analyzing patients with sarcoma (Tab. 4c). Only two patients revealed MAGE-2 and 3/6 expression, while the expression of the different MAGE genes in BM aspirates could not be reproduced. Further, we analyzed 12 patients with advanced and metastatic malignant melanoma using the sensitive MAGE RT-PCR assay. Expression of at least one MAGE gene was observed in only 5 patients with positive results for MAGE-1,2,3/6 and 12 in two samples and MAGE-4 in one sample. The failure to detect circulating cells in patients with localized or even advanced disease seems to indicate the bone marrow as preferential indicator compartment for detecting disseminated tumor cells.

EXAMPLE 9
Different Expression of MAGE-genes in the Primary Tumor of Prostate Cancer Patients Total RNA was prepared primary tumors according to Chomczynski, Analytical Biochemistry 162 (1987) 156–159. Subsequently cDNA was synthesized as described in Example 6. As shown in Table 6, 7 of 20 tumors were positive for MAGE-1, 6 of 20 tumors for MAGE 2 and -12, respectively, 10 of 20 tumors for MAGE 3/6 and 4 of 20 for MAGE-4; overall, 14 of 20 tumors (70%) were positive for at least one MAGE gene product.

EXAMPLE 10
Different Expression of MAGE-genes in the Primary Tumor and in the Bone Marrow of the Same Patient as Determined by the Method of the Invention Total RNA was prepared from the primary tumor of sarcoma patient H. M. (see also Tab. 4c) according to Chomczynski, Analytical Biochemistry 162 (1987) 156–159. Subsequently cDNA was synthesized as described in Example 3 followed by a one-step PCR with 35 cycles for MAGE 1, 2, 3/6, 4 and 12 as described in Example 6.

MAGE-analysis of a bone marrow sample of patient H. M. was carried out according to the method of the invention. Analysis of the primary tumor (results are shown in FIG. 15) revealed predominant expression of MAGE-1 and only weak and inconsistent expression of other MAGE-genes including MAGE-4 and 12. Analysis of the bone marrow, however, only revealed the expression of Mage-4 and -12, but no expression at all of MAGE-1 (Tab. 4c). Thus, the MAGE-expression pattern of systemically disseminated tumor cells does not necessarily match with that of the corresponding primary tumor. Therefore, therapeutic approaches according to claim 5, to eliminate systemically disseminated tumor cells thus preventing future distant metastasis should be preferably based on the analysis of the MAGE-expression pattern of said cells in an appropriate indicator tissue like bone marrow, rather than on analysis of the MAGE-expression pattern of the primary tumor.

EXAMPLE 11
Risk Analysis of Prostate Cancer Patients

In 18 of 30 prostate cancer patients disseminated tumor cells could be detected by bone marrow analysis according to the method of the invention. Patients were regarded MAGE-positive when at least one specific PCR-product for MAGE-1, -2, -3/6, -4 or -12 was detectable in at least one of two bone marrow aspirates taken from the right and left iliac crest, respectively. Clinical data of the patients are listed in Table 7 and 4a (In Table 7 the same 30 prostate cancer patients are listed as in Table 4a. However, as Table 4a contains more preliminary clinical data, there are some discrepancies to Table 7 with regard to tumor staging and grading. Furthermore, the PSA values given in Tab. 4a are those at the time of bone marrow aspiration, and therefore not identical with the initial PSA values at the time of first diagnosis of prostate cancer as given in Tab. 7. Finally, reevaluation of the CK-immunocytochemistry data revealed positive results for the left and negative results for the right bone marrow aspiration samples of patients SC.FR. and LE.DI., respectively; in addition, patient JU.HA. turned out to be CK-positive for both aspiration sites. For the risk analysis of prostate cancer patients data were exiucively taken from Table 7). MAGE-expression was analysed in 22 of the 30 patients, at the time of first diagnosis of prostate cancer or during neoadjuvant therapy of their primary tumor prior to curatively intended prostateclomy or radiation (results are shown in FIG. 4a). The remaining 8 patients analyzed, had progressive disease at the time of analysis as defined by an increasing blood concentration of PSA or by a local relapse; none of these patients, however, had clinical signs of distant metastasis at the time of MAGE-analysis. As it is well established in the art, these patients have a very high risk of future distant metastasis (Zietman, Cancer Supplement 71 (1993), 959–969; Fuks, Int. J. Radiation Oncology Biol. Phys. 21 (1991), 537–547; Pound, Urol. Clin. North Am 24 (1997), 395–406); thus it would be expected that most of them have already undergone systemic dissemination of cancer cells at the time of MAGE-analysis, when clinical evident distant metastasis has not yet developed but is likely to grow out of these disseminated single tumor cells in the future. Indeed, 7 of these 8 patients (87.5%) highly at risk of distant metastasis proved to be MAGE-positive. In contrast, only 11 of 22 patients (50.0%) analyzed in temporal association with their primary tumor, and thus representing both high and low risk patients according to future distant metastasis, were found to be MAGE-positive. Interestingly, only 22.7% of the patients in the latter group (5/22) were found to be MAGE-positive for both aspiration sites, compared to 50% in the high risk group (4/8). These data indicate, that detectable MAGE-expression in at least one bone marrow sample is associated with a high risk of future distant metastasis most probably due to the presence of systemically disseminated tumor cells. Thus, a subgroup of patients suffering from cancer and especially from prostate cancer being highly at risk of future distant metastasis may be identified by the method of the invention. This subgroup may be preferentially subjected to adjuvant cancer therapy according to claim 5 or any other adjuvant approach in order to prevent the outgrowth of distant metastases from systemically disseminated single cancer cells.

TABLE 1

Synthetic oligonucleotide primers for the nested RT-PCR amplification of the different MAGE genes and the conventional RT-PCR amplification of PSA and p53.

| | UPSTREAM AND DOWNSTREAM PRIMER OF THE | |
|---|---|---|
| GENES | EXTERNAL AMPL. | INTERNAL AMPL. |
| MAGE-1 | 5'-gtagagttcggccgaaggaac-3' | 5'-tagagttcggccgaaggaac-3' |
|  | 5'-caggagctgggcaatgaagac-3' | 5'-ctgggcaatgaagacccaca-3' |
| MAGE-2 | 5'-cattgaaggagaagatctgcct-3' | 5'-cattgaaggagaagatcgcct-3' |
|  | 5'-gagcagaagaggaagaagcggt-3' | 5'-caggcttgcagtgctgactc-3' |
| MAGE-3/6 | 5'-gaagccggcccaggctcg-3' | 5'-ggctcggtgaggaggcaag-3' |
|  | 5'-gatgactctggtcagggcaa-3' | 5'-gatgactctggtcagggcaa-3' |

TABLE 1-continued

Synthetic oligonucleotide primers for the nested RT-PCR amplification of the different MAGE genes and the conventional RT-PCR amplification of PSA and p53.

UPSTREAM AND DOWNSTREAM PRIMER OF THE

| GENES | EXTERNAL AMPL. | INTERNAL AMPL. |
|---|---|---|
| MAGE-4 | 5'-caccaaggagaagatctgcct-3' | 5-caccaaggagaagatctgcct-3' |
|  | 5'-tcctcagtagtaggagcctgt-3' | 5'-caggcttgcagtgctgactct-3' |
| MAGE-12 | 5'-tccgtgaggaggcaaggttc-3' | 5'-tccgtgaggaggcaaggttc-3' |
|  | 5'-atcggattgactccagagagta-3' | 5'-gagcctgcgcacccaccaa-3' |
| PSA |  | 5'-cttgtagcctctcgtggcag-3' |
|  |  | 5'-gaccttcatagcatccgtgag-3' |
| p53 |  | 5'-ggatgacagaaacacttttcg-3' |
|  |  | 5'-tcagctctcggaacatctc-3' |

TABLE 2

Specificity of RT-PCR Analyses of hematopoietic tissue from non-carcinoma control patients. Data are presented as positive bone marrow aspirates or PBL over total number of specimens assessed.

| MARKER GENE | BONE MARROW | BLOOD |
|---|---|---|
| 1. Tumor associated and histogenetic differentiation markers: | | |
| CEA (Carcinoembryonic Antigen) | 5/19 | n.d. |
| erbB2 | 5/7 | n.d. |
| erbB3 | 6/7 | n.d. |
| EGP-40 (Epithelial Glycoprotein-40) | 53/53 | n.d. |
| Desmoplakin I | 5/5 | n.d. |
| Cytokeratin-18 | 5/7 | n.d. |
| PIP (Prolactin-inducible Protein) | 3/31 | n.d. |
| PSM (Prostate-Specific Membrane Antigen) | 4/9 | n.d. |
| PSA (Prostate-Specific Antigen) | 0/53 | 0/20 |
| 2. Tumorspecific Markers: | | |
| MAGE - 1 | 0/20 | 0/20 |
| MAGE - 2 | 0/20 | 0/20 |
| MAGE - 3/6 | 0/20 | 0/20 |
| MAGE - 4 | 0/20 | 0/20 |
| MAGE - 12 | 0/20 | 0/20 |

TABLE 3

Expression of the different MAGE genes by manhant tumor cell lines evaluated by specific RT-PCR amplification. Different levels of expression as deduced by band intensity of PCR products are represented by (+) or +. Absence of PCR product is indicated by -.

|  | Mage-1 | Mage-2 | Mage-3/6 | Mage-4 | Mage-12 |
|---|---|---|---|---|---|
| 1A. Tumors derived of ekto-/endodermal origin | | | | | |
| MCF-7 (breast) | + | - | + | - | + |
| BT 20 (breast) | + | + | + | + | + |
| SkBr 3 (breast) | + | - | + | - | + |
| MDA-MB (breast) | - | + | + | - | + |
| LNCaP (prostate) | + | - | + | - | + |
| SkCo (colorectal) | + | - | + | - | (+) |
| HT 29 (colorectal) | + | + | + | (+) | + |
| LS 180 (colorectal) | + | + | + | + | + |
| SW 480 (colorectal) | - | - | - | - | + |
| A 498 (kidney) | - | - | - | - | - |
| CaKi I (kidney) | + | - | - | - | - |
| HEP B 3 (hepar) | + | + | + | - | + |
| HEP G 2 (hepar) | + | - | - | - | - |
| PANC-TU (pancreas) | + | + | - | (+) | + |
| KATO (stomach) | + | + | + | - | + |
| A 427 (lung) | + | + | + | + | + |
| A 431 (epidermoidcarcinoma) | + | + | + | + | + |
| 1B. Tumors derived of neuroektodermal origin | | | | | |
| A 172 (glioblastoma) | + | - | + | - | + |
| U 138 (glioblastoma) | + | + | - | - | + |
| MEL-JUSO (melanoma) | + | + | + | + | + |
| MEL-MEI (melanoma) | + | + | + | - | + |
| A 375 (melanoma) | + | + | - | (+) | + |
| MZ-2 MEL (melanoma) | + | (+) | + | + | + |
| 2. Tumors derived of mesodermal origin | | | | | |
| HT 1080 (fibrosarcoma) | + | + | + | + | + |
| LB-23 SAR (fibrosarcoma) | + | - | + | + | (+) |
| U 937 (lymphoma) | + | + | + | - | + |
| RAJI (Burkitt-lymphoma) | - | - | - | - | + |
| K 562 (erythroleukemia) | + | + | + | (+) | + |

TABLE 4

Clinical data and results (MAGE and PSA RT-PCR, CK-immunocytochemistry) on patients with
a) prostate cancer

| PATIENT | TUMOR SIZE | TUMOR GRADE | PSA LEVEL | ANTI-ANDR. THER. | ASPIR. SITE | MAGE-1 | MAGE-2 | MAGE-3/6 | MAGE-4 | MAGE-12 | PSA | CK-IMMUNO | P.B. ANAL. |
|---|---|---|---|---|---|---|---|---|---|---|---|---|---|
| SC. AU. | C/T3T4 | 3 | 8.1 | y | rc | − | − | − | − | − | − | − | n.d. |
|  |  |  |  |  | lc | + | + | − | − | − | − | + |  |
| SE. NI. | C/T3T4 | 2 | 13 | y | rc | − | − | − | − | − | + | + | MAGE-2 |
|  |  |  |  |  | lc | + | − | − | − | − | − | − |  |
| BA. HE. | A/T1 | 2 | 5.4 | y | rc | + | − | + | + | − | − | + | — |
|  |  |  |  |  | lc | + | − | + | + | − | − | − |  |
| RI. ER. | D/T4 | 3 | 144 | y | rc | + | − | − | + | − | + | + | — |
|  |  |  |  |  | lc | − | − | + | − | − | − | − |  |
| SC. FR. | D/T3T4 | 1 | 8.4 | y | rc | − | − | − | − | − | + | + | n.d. |
|  |  |  |  |  | lc | − | − | − | + | − | − | − |  |
| LE. DI. | B/T1T2 | 2 | 15.1 | y | rc | − | − | − | − | − | + | + | — |
|  |  |  |  |  | lc | + | − | − | − | − | − | − |  |
| WO. JA. | C/T3T4 | 3 | 5.92 | y | rc | − | + | − | − | − | − | − | n.d. |
|  |  |  |  |  | lc | − | − | + | − | − | − | − |  |
| BE. WA. | A/T1 | 2 | 6.42 | y | rc | − | − | − | − | − | − | − | — |
|  |  |  |  |  | lc | − | − | − | − | − | − | − |  |
| GE. CH. | A/T1 | 1 | 4.4 | y | rc | − | − | + | − | − | − | − | — |
|  |  |  |  |  | lc | + | − | − | − | − | − | − |  |
| HE. RU. | C/T3T4 | 2 | 7.8 | y | rc | − | − | − | + | − | − | − | n.d. |
|  |  |  |  |  | lc | − | − | + | − | − | − | − |  |
| KN. DI. | C/T3T4 | 2 | 23.3 | y | rc | − | − | − | − | + | + | − | MAGE-1 + 3.6 |
|  |  |  |  |  | lc |  |  |  |  |  |  |  |  |
|  |  |  |  |  | + | − | − | − | − | + | − |  |  |
| ME. JO. | C/T3T4 | 2 | 134 | y | rc | − | − | − | − | − | − | − | — |
|  |  |  |  |  | lc | − | − | − | − | − | − | − |  |
| JU. HA. | C/T3T4 | 1 | 5.25 | y | rc | − | − | − | − | − | − | + | n.d. |
|  |  |  |  |  | lc | − | − | − | − | − | − | − |  |
| HE. HJ. | B/T2 | 2 | 8.18 | y | rc | − | − | − | − | − | − | + | n.d. |
|  |  |  |  |  | lc | − | − | − | − | − | − | − |  |
| PF. LO. | A/T1 | 2 | 9.51 | y | rc | − | − | − | − | − | − | − | n.d. |
|  |  |  |  |  | lc | − | − | − | − | − | − | − |  |
| SC. EU. | C/T3T4 | 1 | 25 | y | rc | − | − | − | − | − | − | − | n.d. |
|  |  |  |  |  | lc | − | − | − | − | − | − | − |  |
| SC. GU. | C/T3T4 | 2 | 11.3 | y | rc | − | − | − | − | − | − | − | n.d. |
|  |  |  |  |  | lc | − | − | − | − | − | − | − |  |
| KU. WI. | A/T1 | 1 | 3.8 | y | rc | − | − | − | − | − | − | − | — |
|  |  |  |  |  | lc | − | − | − | − | − | − | − |  |
| RI. FE. | A/T1 | 2 | 6.82 | y | rc | + | − | − | − | − | − | + | n.d. |
|  |  |  |  |  | lc | − | − | − | − | − | − | − |  |
| ST. EB. | A/T1 | 2 | 9.14 | n | rc | − | − | − | − | − | − | − | n.d. |
|  |  |  |  |  | lc | − | − | − | − | + | − | − |  |
| SC. HO. | C/T3T4 | 3 | 38.2 | y | rc | − | − | − | + | + | + | − | — |
|  |  |  |  |  | lc | + | − | − | − | − | + | − |  |
| FE. KU. | C/T3T4 | 3 | 24 | n | rc | + | + | − | − | − | − | − | n.d. |
|  |  |  |  |  | lc | − | − | − | − | − | − | − |  |
| LU. VO. | C/T3T4 | 2 | 9.11 | y | rc | − | − | − | − | + | + | − | n.d. |
|  |  |  |  |  | lc | − | − | − | − | + | − | − |  |
| ZO. JO. | C/T3T4 | 2 | 13 | y | rc | + | − | − | − | + | + | − | — |
|  |  |  |  |  | lc | + | − | − | − | − | + | − |  |
| MA. GU. | C/T3T4 | 2 | 20.4 | y | rc | − | − | − | − | − | − | − | n.d. |
|  |  |  |  |  | lc | − | − | − | − | − | − | − |  |
| BA. GI. | C/T3T4 | 2 | 4.16 | y | rc | − | − | − | − | − | − | − | n.d. |
|  |  |  |  |  | lc | − | − | − | − | − | − | − |  |
| WI. JA. | C/T3T4 | 2 | 8.3 | y | rc | − | − | − | − | − | − | − | n.d. |
|  |  |  |  |  | lc | + | − | − | − | − | − | − |  |
| AK. HA. | C/T3T4 | 2 | 18.1 | y | rc | − | − | − | − | − | − | − | n.d. |
|  |  |  |  |  | lc | − | − | − | − | − | − | − |  |
| BI. GU. | B/T2 | 2 | 35.6 | y | rc | − | − | − | + | + | − | − | — |
|  |  |  |  |  | lc | − | − | − | − | − | − | − |  |
| HI. ER. | B/T2 | 1 | 9.1 | n | rc | − | − | − | − | − | − | − | n.d. |
|  |  |  |  |  | lc | − | − | − | − | − | − | − |  |

TABLE 4-continued

Clinical data and results (MAGE and PSA RT-PCR, CK-immunocytochemistry) on patients with b) lung cancer

| PATIENT | HISTOLOGY | STAGING | BONE MARROW ANALYSES | | | | | |
|---|---|---|---|---|---|---|---|---|
| | | | MAGE-1 | MAGE-2 | MAGE-3/6 | MAGE-4 | MAGE-12 | CK-IMMUNO |
| VO. KL. | SQUAMOUS | T2N0M0 | + | − | + | + | + | + |
| AR-JR. | BLASTOMA | T2N1M0 | − | − | − | − | − | + |
| WE. AL. | SQUAMOUS | T2N1M0 | − | − | − | − | − | + |
| RO. AD. | SQUAMOUS | T4N0M0 | − | + | − | − | − | + |
| GA. AB. | SQUAMOUS | T2N2M0 | − | − | − | − | + | + |
| FI. RI. | SCLC | T2N1M0 | + | − | − | − | + | − |
| RE. LU. | ADENO | T2N2M0 | − | − | + | + | − | − |
| HE. JO. | SQUAMOUS | T2N1M0 | − | + | − | − | − | + |
| KU. LU. | ADENO | T4N2M0 | − | − | − | + | − | − |
| KL. JU. | ADENO | T1N0M0 | − | − | − | − | − | − |
| LÖ. MA. | ADENO | T4N3M0 | − | + | − | − | − | − |
| HA. AN. | ADENO | T1N0M0 | − | − | − | − | − | − |
| CR. GO. | SQUAMOUS | T2N0M0 | − | + | − | − | − | + |
| DE. IV. | SQUAMOUS | T1N1M0 | + | − | + | − | − | + |
| BE. FR. | SQUAMOUS | T2N1M0 | − | − | − | − | − | − |
| MA. RO. | SQUAMOUS | T2N0M0 | − | − | − | − | − | − |
| HA. HI. | ADENO | T2N0M0 | − | − | − | − | − | − |
| HO. FR. | SQUAMOUS | T4N3M0 | − | − | − | − | − | − |
| MA. JO. | ADENO | T2N1M0 | − | − | − | − | − | − |
| LA. BR. | SQUAMOUS | T2N1M0 | − | − | − | − | − | − |
| IN. FR. | SARCOMA | T3N0M0 | − | − | − | − | − | − |
| LA. AL. | ADENO | T2N2M0 | − | − | − | − | − | − |
| SC. JO. | ADENO | T2N2M0 | − | − | − | − | − | − |
| ZI. JO. | SQUAMOUS | T3N1M0 | + | − | − | − | − | − |
| KR. WI. | SQUAMOUS | T2N1M0 | − | − | − | − | − | − |
| NI. OS | LARGE-CELL | T2N0M0 | + | − | − | − | + | − |
| SO. JO. | SQUAMOUS | T2N2M0 | − | − | − | − | − | − |
| NE. WI. | SQUAMOUS | T2N2M0 | − | − | − | − | − | − |
| BA. MA. | SQUAMOUS | T4N1M0 | − | − | − | − | − | − |
| BE. FE. | SQUAMOUS | T2N0M0 | − | − | − | − | − | − |
| MA. RI. | SQUAMOUS | T3N2M0 | − | − | − | − | − | − |
| IV. MA. | SQUAMOUS | T2N0M0 | − | − | − | − | − | − |
| PO. MA. | LARGE-CELL | T2N1M0 | − | − | − | − | − | − |
| SC. JO. | ADENO | T2N1M0 | − | − | − | − | − | − |

Clinical data and results of MAGE RT-PCR on patients with c) sarcoma

| PATIENT | HISTOLOGY | LOCALIZATION OF PRIMARY TUMOR | M-STAGE | BONE MARROW ANALYSES | | | | | PB ANALSES |
|---|---|---|---|---|---|---|---|---|---|
| | | | | MAGE-1 | MAGE-2 | MAGE-3/6 | MAGE-4 | MAGE-12 | |
| H. G. | SYNOVIAL SARCOMA | RIGHT FEMOR | M1 | − | − | − | − | − | — |
| R. T. | LEIOMYOSARCOMA | RIGHT FEMOR | M1 | − | − | − | − | − | — |
| R. R. | EPITHELOID SARCOME | PARAVERTEBRAL | M0 | − | − | − | − | − | — |
| L. G. | LEIOMYOSARCOMA | PELVIS MINOR | M1 | + | − | − | − | − | — |
| D. K. | EWING'S SARCOMA | MULTILOCULAR | M0 | − | − | − | + | + | — |
| H. M. | UNDIFFERENTIATED SARCOMA | CARDIAC STOMACH | M0 | − | − | − | + | + | — |
| T. L. | RHABDOMYOSARCOMA | PELVIS MINOR | M1 | + | + | + | + | + | MAGE-2 |

TABLE 5

Analyses of bone marrow aspirates of 27 healthy persons (= allogeneic bone marrow donors). Data are presented as negative and positive results in RT-PCR of total number of specimens assessed.

| MARKER GENE | BONE MARROW | |
|---|---|---|
| | PCR-pos. | PCR-neg. |
| MAGE-1 | 0 | 27 |
| MAGE-2 | 0 | 27 |
| MAGE-3/6 | 0 | 27 |
| MAGE-4 | 0 | 27 |
| MAGE-12 | 0 | 27 |

TABLE 6

Expression of the different MAGE genes by primary tumors of 20 patients with prostate cancer. Evaluation was obtained by specific RT-PCR amplification of native malignant prostatic tissue. Data are presented as negative and positive results in RT-PCR of total number of specimens assessed.

| MARKER GENE | PROSTATE TUMOR | |
|---|---|---|
| | PCR-pos. | PCR-neg. |
| MAGE-1 | 7 | 13 |
| MAGE-2 | 6 | 14 |
| MAGE-3/6 | 10 | 10 |
| MAGE-4 | 4 | 16 |

TABLE 6-continued

Expression of the different MAGE genes by primary tumors of 20 patients with prostate cancer. Evaluation was obtained by specific RT-PCR amplification of native malignant prostatic tissue. Data are presented as negative and positive results in RT-PCR of total number of specimens assessed.

| MARKER GENE | PROSTATE TUMOR | |
| --- | --- | --- |
| | PCR-pos. | PCR-neg. |
| MAGE-12 | 6 | 14 |
| at least one MAGE | 14 | 6 |

3=poorly differentiated), TNM-stage related to biopsy and lymphadenectomy (=b) or related to prostatectomy and lymphadenectomy (=p), PSA-level prior to therapy (=initial PSA), results of immunocytochemistry and RT-PCR, time of aspiration (0=bone marrow aspiration at the time of progressive disease but without clinically evident distant metastasis, x=bone marrow aspiration at the time of first diagnosis of prostate cancer or during neoadjuvant therapy of the primary tumor prior to curatively intended prostatectomy or radiation), treatment modality (A=neoadjuvant antiandrogen therapy and subsequent prostatectomy, B=neoadjuvant antiandrogen therapy and subsequent radiation, C=transurethral resection, D=primary antiandrogen therapy, E=prostatectomy and adjuvant antiandrogen therapy, F=neoadjuvant antiandrogen therapy plus

TABLE 7

| Patient | Clinical Stage | Time of first diagnosis | Stage/Grade | Histology/Grade | CK l/r | initial PSA-Level ($\mu$g/l) | PSA-PCR l/r | Bone Marrow PCR-Analyses using MAGE Genes | | | | | Time of aspiration | Treatment | Follow-up |
| --- | --- | --- | --- | --- | --- | --- | --- | --- | --- | --- | --- | --- | --- | --- | --- |
| | | | | | | | | 1 l/r | 2 l/r | 3/6 l/r | 4 l/r | 12 l/r | | | |
| SC. AU. | C | 12/1994 | $T_4N_0M_0$/p | Adeno/2 | +/− | 11.8 | −/− | +/− | +/− | −/− | −/− | −/− | 0 | A | BCR 5/96 |
| SE. NI. | C | 6/1996 | $T_3N_2M_0$/p | Adeno/2 | −/+ | 11.6 | −/+ | +/− | −/− | −/− | −/− | −/− | x | A | NR 11/97 |
| BA. HE. | B | 9/1995 | $T_2N_2M_0$/p | Adeno/2 | −/+ | 54 | −/− | +/+ | −/− | +/+ | +/+ | −/− | x | A | NR 1/98 |
| RI. ER. | D | 12/1994 | $T_4N_2M_0$/b | Adeno/3 | −/+ | 144.4 | −/+ | −/+ | −/− | +/− | −/+ | −/− | x | D | BCR 96 DM 97 |
| SC. FR. | C | 6/1994 | $T_2N_2M_0$/p | Adeno/1 | +/− | 99 | −/+ | −/− | −/− | −/− | +/− | −/− | 0 | A | BCR 11/95 |
| LE. DI. | B | n.a. | $T_0N_2M_0$/p | Adeno/0 | +/− | 15.1 | −/+ | +/− | −/− | −/− | −/− | −/− | x | A | n.a. |
| WO. JA. | B | 12/1991 | $T_3N_2M_0$/b | Adeno/3 | −/− | n.a. | −/− | −/− | −/+ | +/− | −/− | −/− | 0 | D | BCR 5/96 |
| BE. WA. | A | 10/1995 | $T_2N_2M_0$/p | Adeno/2 | −/− | 9.51 | −/− | −/− | −/− | −/− | −/− | −/− | x | A | NR 3/97 |
| GE. CH. | C | 1992 | $T_3N_1M_0$/p | Adeno/3 | −/− | n.a. | −/− | +/− | −/− | −/+ | −/− | −/− | 0 | E | LR 96, DM 97 |
| HE. RU. | C | 7/1994 | $T_3N_2M_0$/p | Adeno/3 | −/− | n.a. | −/− | −/− | −/− | +/− | −/+ | −/− | 0 | G | BCR 6/96 |
| KN. DI. | C | 10/1992 | $T_3N_2M_0$/p | Adeno/2 | −/− | n.a. | +/+ | +/− | −/− | −/− | −/− | −/+ | 0 | A | BCR + LR /96 |
| ME. JO. | C | 7/1996 | $T_3N_0M_0$/b | Adeno/2 | −/− | 134 | −/− | −/− | −/− | −/− | −/− | −/− | x | B | NR 1/98 |
| JU. HA. | C | 7/1996 | $T_2N_2M_0$/p | Adeno/2 | +/+ | 5.25 | −/− | −/− | −/− | −/− | −/− | −/− | x | A | NR 1/98 |
| WE. HJ. | B | 7/1996 | $T_2N_2M_0$/b | Adeno/2 | −/+ | 8.2 | −/− | −/− | −/− | −/− | −/− | −/− | x | n.a. | n.a. |
| PF. LO. | C | 12/1995 | $T_2N_0M_0$/p | Adeno/2 | −/− | 9.27 | −/− | −/− | −/− | −/− | −/− | −/− | x | A | n.a. |
| SC. EU. | C | 1992 | $T_3N_2M_0$/p | Adeno/2 | −/− | n.a. | −/− | −/− | −/− | −/− | −/− | −/− | 0 | A | BCR + LR 96 |
| SC. GU. | A | 10/1995 | $T_0N_2M_0$/p | Adeno/0 | −/− | 15.7 | −/− | −/− | −/− | −/− | −/− | −/− | x | A | LR 11/97 |
| KU. WI. | C | 4/1996 | $T_2N_2M_0$/p | Neuro/3 | −/− | 0.777 | −/− | −/− | −/− | −/− | −/− | −/− | x | F | LR + DM 97 |
| RI. FE. | A | 3/1996 | $T_4N_2M_0$/p | Adeno/2 | −/+ | 41.4 | −/− | −/+ | −/− | −/− | −/− | −/− | x | A | iBCR 1/98 |
| ST. EB. | A | 5/1996 | $T_1N_1M_0$/t | Adeno/2 | −/− | 9.14 | −/− | −/− | −/− | −/− | −/− | +/− | x | C | BCR 3/98 |
| SC. HO. | C | 8/1995 | $T_4N_2M_0$/p | Adeno/3 | −/− | 56.3 | +/+ | +/− | −/− | −/− | −/+ | −/+ | x | A | BCR 3/98 |
| FE. KU. | C | 7/1996 | $T_3N_2M_0$/p | Adeno/3 | −/− | 23.8 | −/− | −/+ | −/+ | −/− | −/− | −/− | x | A | n.a. |
| LU. VO. | C | 7/1996 | $T_3N_2M_0$/p | Adeno/2 | −/− | 14.5 | −/+ | −/− | −/− | −/− | −/− | +/+ | x | A | NR 10/97 |
| ZO. JO. | C | 1/1996 | $T_2N_2M_0$/p | Adeno/2 | −/− | 13.0 | +/+ | +/+ | −/− | −/− | −/− | −/+ | x | A | iBCR 3/98 |
| MA. GU. | C | 5/1996 | $T_0N_2M_0$/p | Adeno/0 | −/− | 20.4 | −/− | −/− | −/− | −/− | −/− | −/− | x | A | NR 1/98 |
| BA. GI. | C | 3/1996 | $T_3N_2M_0$/p | Adeno/1 | −/− | 4.2 | −/− | −/− | −/− | −/− | −/− | −/− | x | B | NR 5/97 |
| WI. JA. | C | 7/1995 | $T_2N_2M_0$/p | Adeno/2 | −/− | 5.31 | −/− | +/− | −/− | −/− | −/− | −/− | 0 | A | BCR + LR 96 |
| AK. HA. | C | 8/1995 | $T_2N_0M_0$/p | Adeno/2 | −/− | 14.0 | −/− | −/− | −/− | −/− | −/− | −/− | x | A | NR 11/97 |
| BI. GU. | B | 5/1996 | $T_2N_0M_0$/p | Adeno/2 | −/− | 31.5 | −/− | −/− | −/− | −/− | −/+ | −/+ | x | A | NR 12/97 |
| HI. ER. | C | 5/1996 | $T_3N_2M_0$/p | Adeno/2 | −/− | 15.2 | −/− | −/− | −/− | −/− | −/− | −/− | x | A | NR 2/98 |

Table 7— legend

Clinical data of 30 patients with prostate cancer and the corresponding results of MAGE RT-PCR, PSA RT-PCR and CK-Immunocytochemistry as obtained by the analysis of bone marrow samples from the right and left iliac crest, respectively. Table lists: patients, clinical stage A-D, time of first diagnosis, histology (adenocarcinoma=adeno, neuroendocrine carcinoma=neuro) and corresponding grading (1=well differentiated, 2=moderately differentiated, 3=poorly differentiated), chemotherapy, and subsequent prostatectomy, G=prostatectomy), as well as time and result of last clinical follow-up (NR=no relapse, BCR=biochemical relapse as defined by continuously PSA levels over prolonged periods of time, iBCR=initially increasing PSA level over a short period of time prior to end of follow-up, LR=local relapse, DM=clinically evident distant metastasis). n.a.=not available.

What is claimed is:

1. A primer which specifically hybridizes to a nucleic acid molecule complementary to a messenger RNA transcribed from a gene encoding a MAGE tumor-specific antigen or a fragment thereof or to a complementary strand thereof, said primer being selected from primers having at least 15 contiguous 3'-end nucleotides as set forth in the sequences provided in one of the following groups of primers:

(a)
| | |
|---|---|
| 5'-gtagagttcggccgaaggaac-3' | (SEQ ID NO: 1) |
| 5'-caggagctgggcaatgaagac-3' | (SEQ ID NO: 2) |
| 5'-cattgaaggagaagatctgcct-3' | (SEQ ID NO: 3) |
| 5'-gagtagaagaggaagaagcggt-3' | (SEQ ID NO: 4) |
| 5'-gaagccggcccaggctcg-3' | (SEQ ID NO: 5) |
| 5'-gatgactctggtcagggcaa-3' | (SEQ ID NO: 6) |
| 5'-caccaaggagaagatctgcct-3' | (SEQ ID NO: 7) |
| 5'-tcctcagtagtaggagcctgt-3' | (SEQ ID NO: 8) |
| 5'-tccgtgaggaggcaaggttc-3' | (SEQ ID NO: 9) |
| 5'-atcggattgactccagagagta-3' | (SEQ ID NO: 10); or |

(b)
| | |
|---|---|
| 5'-tagagttcggccgaaggaac-3' | (SEQ ID NO: 11) |
| 5'-ctgggcaatgaagacccaca-3' | (SEQ ID NO: 12) |
| 5'-cattgaaggagaagatctgcct-3' | (SEQ ID NO: 13) |
| 5'-caggcttgcagtgctgactc-3' | (SEQ ID NO: 14) |
| 5'-ggctcggtgaggaggcaag-3' | (SEQ ID NO: 15) |
| 5'-gatgactctggtcagggcaa-3' | (SEQ ID NO: 16) |
| 5'-caccaaggagaagatctgcct-3' | (SEQ ID NO: 17) |
| 5'-caggcttgcagtgctgactct-3' | (SEQ ID NO: 18) |
| 5'-tccgtgaggaggcaaggttc-3' | (SEQ ID NO: 19) |
| 5'-gagcctgcgcacccaccaa-3' | (SEQ ID NO: 20). |

2. The primer according to claim 1 which is a primer depicted in either group (a) or group (b).

3. A diagnostic composition comprising at least 4 primers according to claim 1 wherein said at least four primers hybridize to strands of opposite orientation of at least two different nucleic acid molecules wherein strands of one orientation are complementary to the mRNA transcribed from the genes of at least two different MAGE tumor-specific antigens.

4. A method of detecting disseminated MAGE-expressing tumors cells indicative of a cancerous condition in a patient comprising:
(a) performing PCR on cDNA obtained from mRNA from one or more patient samples using at least two primers according to claim 1; and (b) detecting one or more PCR products related to MAGE-1, MAGE-2, MAGE-3, MAGE-4, MAGE-6 or MAGE-12, thereby detecting disseminated MAGE-expressing tumor cells.

5. A method of preparing a tumor adjuvant vaccine comprising the following steps:
(a) performing PCR on cDNA obtained from mRNA from one or more patient samples using at least four primers according to claim 1 hybridizing pair-wise to strands of opposite orientation of at least two different nucleic acid molecules wherein strands of one orientation are complementary to the messenger RNA transcribed from the genes of at least two different MAGE tumor-specific antigens;
(b) detecting resulting PCR products; and
(c) using at least one MAGE-gene product whose expression is indicated by the detection of the PCR products, including whole MAGE-antigens MAGE-transfected host cells, or MAGE-encoding nucleotide sequences for the preparation of an adjuvant tumor vaccine.

6. The method according to claim 4 or 5 wherein said cDNA is obtained by:
(a) preparing mRNA from one or more samples removed from said patient; and
(b) reverse trans ng said mRNA.

7. The method according to any one of claims 4 to 6 wherein said PCR is nested PCR.

8. The method according to any one of claims 4 to 5, wherein preparation of said mRNA comprises the following steps:
(a) immediately lysing the sample in buffer essentially completely avoiding RNA-degradation; and
(b) optionally centrifuging the mRNA obtained in the lysate through a cushion of an RNAse-inhibiting agent, preferably cesium trifluoroacetate.

9. The method according to any one of claims 4 to 8 wherein said cancerous condition is related to prostate cancer, non-small or small lung cancer, sarcoma, malignant melanoma, breast cancer or colorectal cancer.

10. The method according to any one of claims 4 to 7, wherein said primers hybridize to 2 to 6 different nucleic acid molecules complementary to the mRNA transcribed from the genes of MAGE tumor-specific antigens and the complementary strands thereof.

11. The method according to claim 5 wherein said MAGE tumor-specific antigens are the MAGE-1, -2, -3, -4, -6, or -12 tumor-specific antigens.

12. The method according to any one of claims 4 to 11 wherein said samples are removed from two different aspiration sites.

13. The method according to any one of claims 4 to 12 wherein said samples are bone marrow aspirates.

14. A method of preparing a tumor adjuvant vaccine comprising the following steps:
(a) performing PCR on cDNA obtained from mRNA from one or more patient samples using at least four primers according to claim 1 hybridizing pair-wise to strands of opposite orientation of at least two different nucleic acid molecules wherein strands of one orientation are complementary to the messenger RNA transcribed from the genes of at least two different MAGE tumor-specific antigens;

(b) detecting resulting PCR products; and (c) using at least one MAGE-gene product whose expression is indicated by the detection of the PCR products, wherein the gene product is a whole MAGE protein, for the preparation of an adjuvant tumor vaccine.

15. A primer capable of specifically hybridizing to a nucleic acid molecule complementary to the messenger RNA transcribed from a gene encoding a MAGE tumor-specific antigen or a part thereof or to a complementary strand thereof, said nucleic acid molecule or complementary strand thereof having a sequence selected from:

| | |
|---|---|
| 5'-gttccttcggccgaactctac-3' | (SEQ ID NO: 21); |
| 5'-gtcttcattgcccagctcctg-3' | (SEQ ID NO: 22); |
| 5'-aggcagagatcttctccttcaatg-3' | (SEQ ID NO: 23); |
| 5'-accgcttcttcctcttctactc-3' | (SEQ ID NO: 24); |
| 5'-cgagcctgggccggcttc-3' | (SEQ ID NO: 25); |
| 5'-ttgccctgaccagagtcatc-3' | (SEQ ID NO: 26); |
| 5'-aggcagatcttctccttggtg-3' | (SEQ ID NO: 27); |
| 5'-acaggctcctactactgagga-3' | (SEQ ID NO: 28); |
| 5'-gaaccttgcctcctcacgga-3' | (SEQ ID NO: 29); |
| 5'-tactctctggagtcaatccgat-3' | (SEQ ID NO: 30); |
| 5'-gttccttcggccgaactcta-3' | (SEQ ID NO: 31); |
| 5'-tgtgggtcttcattgcccag-3' | (SEQ ID NO: 32); |
| 5'-aggcagatcttctccttcaatg-3' | (SEQ ID NO: 33); |
| 5'-gagtcagcactgcaagcctg-3' | (SEQ ID NO: 34); |
| 5'-cttgcctcctcaccgagcc-3' | (SEQ ID NO: 35); |
| 5'-ttgccctgaccagagtcatc-3' | (SEQ ID NO: 36); |
| 5'-aggcagatcttctccttggtg-3' | (SEQ ID NO: 37); |
| 5'-agagtcagcactgcaagcctg-3' | (SEQ ID NO: 38); |
| 5'-gaaccttgcctcctcacgga-3' | (SEQ ID NO: 39); and |
| 5'-ttggtgggtgcgcaggctc-3' | (SEQ ID NO :40). |

16. The primer of claim 15, wherein the primer specifically hybridizes to the 15 contiguous 3' nucleotides of the nucleic acid molecules or complementary strands thereof, set out in claim 15.

17. The primer of claim 15, wherein the primer specifically hybridizes to about 10 contiguous 5' nucleotides of the nucleic acid molecules or complementary strands thereof, set out in claim 15.

18. The primer of claim 16, said primer being selected from the group consisting of primers having at least 15 contiguous 3'-end nucleotides from the following nucleic acid sequences:

| | |
|---|---|
| 5'-gtagagttcggccgaaggaac-3' | (SEQ ID NO: 1); |
| 5'-caggagctgggcaatgaagac-3' | (SEQ ID NO: 2); |
| 5'-cattgaaggagaagatctgcct-3' | (SEQ ID NO: 3); |
| 5'-gagtagaagaggaagaagcggt-3' | (SEQ ID NO: 4); |
| 5'-gaagccggcccaggctcg-3' | (SEQ ID NO: 5); |
| 5'-gatgactctggtcagggcaa-3' | (SEQ ID NO: 6); |
| 5'-caccaaggagaagatctgcct-3' | (SEQ ID NO: 7); |
| 5'-tcctcagtagtaggagcctgt-3' | (SEQ ID NO: 8); |
| 5'-tccgtgaggaggcaaggttc-3' | (SEQ ID NO: 9); |
| 5'-atcggattgactccagagagta-3' | (SEQ ID NO: 10); |
| 5'-tagagttcggccgaaggaac-3' | (SEQ ID NO: 11); |
| 5'-ctgggcaatgaagacccaca-3' | (SEQ ID NO: 12); |
| 5'-cattgaaggagaagatctgcct-3' | (SEQ ID NO: 13); |
| 5'-caggcttcagtgctgactc-3' | (SEQ ID NO: 14); |
| 5'-ggctcggtgaggaggcaag-3' | (SEQ ID NO: 15); |
| 5'-gatgactctggtcagggcaa-3' | (SEQ ID NO: 16); |
| 5'-caccaaggagaagatctgcct-3' | (SEQ ID NO: 17); |
| 5'-caggcttcagtgctgactct-3' | (SEQ ID NO: 18); |
| 5'-tccgtgaggaggcaaggttc-3' | (SEQ ID NO: 19); and |
| 5'-gagcctgcgcacccaccaa-3' | (SEQ ID NO: 20). |

19. The primer of claim 15, wherein the primer has a length of between 15 and 25 nucleotides.

20. The primer of claim 15, said primer being selected from the group consisting of primers having at least 15 contiguous 3' nucleotides of the following nucleic acid sequences:

| | |
|---|---|
| 5'-gatgactctggtcagggcaa-3' | (SEQ ID NO: 6); |
| 5'-caccaaggagaagatctgcct-3' | (SEQ ID NO: 7); |
| 5'-tcctcagtagtaggagcctgt-3' | (SEQ ID NO: 8); |
| 5'-tccgtgaggaggcaaggttc-3' | (SEQ ID NO: 9); |
| 5'-atcggattgactccagagagta-3' | (SEQ ID NO: 10); |
| 5'-tagagttcggccgaaggaac-3' | (SEQ ID NO: 11); |
| 5'-ctgggcaatgaagacccaca-3' | (SEQ ID NO: 12); |
| 5'-cattgaaggagaagatctgcct-3' | (SEQ ID NO: 13); |
| 5'-caggcttcagtgctgactc-3' | (SEQ ID NO: 14); |
| 5'-ggctcggtgaggaggcaag-3' | (SEQ ID NO: 15); |
| 5'-gatgactctggtcagggcaa-3' | (SEQ ID NO: 16); |
| 5'-caccaaggagaagatctgcct-3' | (SEQ ID NO: 17); |
| 5'-caggcttcagtgctgactct-3' | (SEQ ID NO: 18); |
| 5'-tccgtgaggaggcaaggttc-3' | (SEQ ID NO: 19); and |
| 5'-gagcctgcgcacccaccaa-3' | (SEQ ID NO: 20). |

* * * * *

UNITED STATES PATENT AND TRADEMARK OFFICE
CERTIFICATE OF CORRECTION

PATENT NO. : 6,475,727 B1
DATED : November 5, 2002
INVENTOR(S) : Kufer and Zippelius It is certified that error appears in the above-identified patent and that said Letters Patent is hereby corrected as shown below:

<u>Title page,</u>
Item [73], delete "Micromet Gesellschaft Fur Biomedizinische Forschung mbH (DE)" and replace with -- Micromet AG (DE) --

Signed and Sealed this

Twentieth Day of May, 2003

JAMES E. ROGAN
*Director of the United States Patent and Trademark Office*

SEQUENCE LISTING

<160> NUMBER OF SEQ ID NOS: 20

<210> SEQ ID NO 1
<211> LENGTH: 21
<212> TYPE: DNA
<213> ORGANISM: Artificial Sequence
<220> FEATURE:
<223> OTHER INFORMATION: oligonucleotide

<400> SEQUENCE: 1
gtagagttcg gccgaaggaa c                                              21

<210> SEQ ID NO 2
<211> LENGTH: 21
<212> TYPE: DNA
<213> ORGANISM: Artificial Sequence
<220> FEATURE:
<223> OTHER INFORMATION: oligonucleotide

<400> SEQUENCE: 2
caggagctgg gcaatgaaga c                                              21

<210> SEQ ID NO 3
<211> LENGTH: 22
<212> TYPE: DNA
<213> ORGANISM: Artificial Sequence
<220> FEATURE:
<223> OTHER INFORMATION: oligonucleotide

<400> SEQUENCE: 3
cattgaagga gaagatctgc ct                                             22

<210> SEQ ID NO 4
<211> LENGTH: 22
<212> TYPE: DNA
<213> ORGANISM: Artificial Sequence
<220> FEATURE:
<223> OTHER INFORMATION: oligonucleotide

<400> SEQUENCE: 4
gagtagaaga ggaagaagcg gt                                             22

<210> SEQ ID NO 5
<211> LENGTH: 18
<212> TYPE: DNA
<213> ORGANISM: Artificial Sequence
<220> FEATURE:
<223> OTHER INFORMATION: oligonucleotide

<400> SEQUENCE: 5
gaagccggcc caggctcg                                                  18

<210> SEQ ID NO 6
<211> LENGTH: 20
<212> TYPE: DNA
<213> ORGANISM: Artificial Sequence
<220> FEATURE:
<223> OTHER INFORMATION: oligonucleotide

<400> SEQUENCE: 6
gatgactctg gtcagggcaa                                                20

<210> SEQ ID NO 7
<211> LENGTH: 21

```
<212> TYPE: DNA
<213> ORGANISM: Artificial Sequence
<220> FEATURE:
<223> OTHER INFORMATION: oligonucleotide

<400> SEQUENCE: 7
caccaaggag aagatctgcc t                                    21

<210> SEQ ID NO 8
<211> LENGTH: 21
<212> TYPE: DNA
<213> ORGANISM: Artificial Sequence
<220> FEATURE:
<223> OTHER INFORMATION: oligonucleotide

<400> SEQUENCE: 8
tcctcagtag taggagcctg t                                    21

<210> SEQ ID NO 9
<211> LENGTH: 20
<212> TYPE: DNA
<213> ORGANISM: Artificial Sequence
<220> FEATURE:
<223> OTHER INFORMATION: oligonucleotide

<400> SEQUENCE: 9
tccgtgagga ggcaaggttc                                      20

<210> SEQ ID NO 10
<211> LENGTH: 22
<212> TYPE: DNA
<213> ORGANISM: Artificial Sequence
<220> FEATURE:
<223> OTHER INFORMATION: oligonucleotide

<400> SEQUENCE: 10
atcggattga ctccagagag ta                                   22

<210> SEQ ID NO 11
<211> LENGTH: 20
<212> TYPE: DNA
<213> ORGANISM: Artificial Sequence
<220> FEATURE:
<223> OTHER INFORMATION: oligonucleotide

<400> SEQUENCE: 11
tagagttcgg ccgaaggaac                                      20

<210> SEQ ID NO 12
<211> LENGTH: 20
<212> TYPE: DNA
<213> ORGANISM: Artificial Sequence
<220> FEATURE:
<223> OTHER INFORMATION: oligonucleotide

<400> SEQUENCE: 12
ctgggcaatg aagacccaca                                      20

<210> SEQ ID NO 13
<211> LENGTH: 22
<212> TYPE: DNA
<213> ORGANISM: Artificial Sequence
<220> FEATURE:
<223> OTHER INFORMATION: oligonucleotide

<400> SEQUENCE: 13
```
cattgaagga gaagatctgc ct                                          22

<210> SEQ ID NO 14
<211> LENGTH: 20
<212> TYPE: DNA
<213> ORGANISM: Artificial Sequence
<220> FEATURE:
<223> OTHER INFORMATION: oligonucleotide

<400> SEQUENCE: 14
caggcttgca gtgctgactc                                             20

<210> SEQ ID NO 15
<211> LENGTH: 19
<212> TYPE: DNA
<213> ORGANISM: Artificial Sequence
<220> FEATURE:
<223> OTHER INFORMATION: oligonucleotide

<400> SEQUENCE: 15
ggctcggtga ggaggcaag                                              19

<210> SEQ ID NO 16
<211> LENGTH: 20
<212> TYPE: DNA
<213> ORGANISM: Artificial Sequence
<220> FEATURE:
<223> OTHER INFORMATION: oligonucleotide

<400> SEQUENCE: 16
gatgactctg gtcagggcaa                                             20

<210> SEQ ID NO 17
<211> LENGTH: 21
<212> TYPE: DNA
<213> ORGANISM: Artificial Sequence
<220> FEATURE:
<223> OTHER INFORMATION: oligonucleotide

<400> SEQUENCE: 17
caccaaggag aagatctgcc t                                           21

<210> SEQ ID NO 18
<211> LENGTH: 21
<212> TYPE: DNA
<213> ORGANISM: Artificial Sequence
<220> FEATURE:
<223> OTHER INFORMATION: oligonucleotide

<400> SEQUENCE: 18
caggcttgca gtgctgactc t                                           21

<210> SEQ ID NO 19
<211> LENGTH: 20
<212> TYPE: DNA
<213> ORGANISM: Artificial Sequence
<220> FEATURE:
<223> OTHER INFORMATION: oligonucleotide

<400> SEQUENCE: 19
tccgtgagga ggcaaggttc                                             20

<210> SEQ ID NO 20
<211> LENGTH: 19
<212> TYPE: DNA
<213> ORGANISM: Artificial Sequence -continued

```
<220> FEATURE:
<223> OTHER INFORMATION: oligonucleotide

<400> SEQUENCE: 20
gagcctgcgc acccaccaa                                            19
```